US006517484B1

(12) United States Patent
Wilk et al.

(10) Patent No.: US 6,517,484 B1
(45) Date of Patent: Feb. 11, 2003

(54) ULTRASONIC IMAGING SYSTEM AND ASSOCIATED METHOD

(75) Inventors: Peter J. Wilk, New York, NY (US); Robert C. Stirbl, New York, NY (US)

(73) Assignee: Wilk Patent Development Corporation, New York, NY (US)

( * ) Notice: Subject to any disclaimer, the term of this patent is extended or adjusted under 35 U.S.C. 154(b) by 0 days.

(21) Appl. No.: 09/514,168

(22) Filed: Feb. 28, 2000

(51) Int. Cl.⁷ .................................................. A61B 8/00
(52) U.S. Cl. ...................................... 600/437; 600/443
(58) Field of Search .............................. 600/437, 443, 600/444, 448; 128/916

(56) References Cited

U.S. PATENT DOCUMENTS

| | | |
|---|---|---|
| 3,552,382 A | 1/1971 | Mount |
| 3,927,662 A | 12/1975 | Ziedonis |
| 4,048,616 A | 9/1977 | Hart et al. |
| 4,149,420 A | 4/1979 | Hutchison et al. |
| 4,315,514 A | 2/1982 | Drewes et al. |
| 4,623,219 A | 11/1986 | Trias |
| 4,646,158 A | 2/1987 | Ohno et al. |
| 4,757,820 A | 7/1988 | Itoh |
| 4,771,786 A | 9/1988 | Iinuma |
| 4,819,649 A | 4/1989 | Rogers et al. |
| 4,991,604 A | 2/1991 | Wurster et al. |
| 5,078,143 A | 1/1992 | Okazaki et al. |
| 5,091,893 A | 2/1992 | Smith et al. |
| 5,099,459 A | 3/1992 | Smith |
| 5,099,848 A | 3/1992 | Parker et al. |
| 5,135,001 A | 8/1992 | Sinofsky et al. |
| 5,163,436 A | 11/1992 | Saitoh et al. |
| 5,167,231 A | 12/1992 | Matsui |
| 5,203,336 A | 4/1993 | Iida et al. |
| 5,391,140 A | 2/1995 | Schaetzle et al. |
| 5,394,877 A | 3/1995 | Orr et al. |
| 5,435,311 A | 7/1995 | Umemura et al. |
| 5,437,278 A | 8/1995 | Wilk |
| 5,448,994 A | 9/1995 | Iinuma |
| 5,488,952 A | 2/1996 | Schoolman |
| 5,526,815 A | 6/1996 | Granz et al. |
| 5,611,343 A | 3/1997 | Wilson |
| 5,611,345 A | 3/1997 | Hibbeln |
| 5,619,999 A | 4/1997 | Von Behren et al. |
| 5,666,953 A | 9/1997 | Wilk |
| 5,865,750 A * | 2/1999 | Hatfiled et al. ............. 600/443 |

(List continued on next page.)

Primary Examiner—Marvin M. Lateef
Assistant Examiner—Maulin Patel
(74) Attorney, Agent, or Firm—R. Neil Sudol; Henry D. Coleman; William J. Sapone

(57) ABSTRACT

An ultrasonic medical imaging system comprises a calibration system, a transducer position determination system and an image formation system. The calibration system adjusts the remaining two systems and is part of the overall medical imaging system. A position determination system may discretely determine positions of sensors or sensor arrays considered as rigid bodies, or may continuously determine a shape of a flexible essentially two-dimensional body or mat in which the sensors or sensor arrays are embedded. The position determination system may be internal to a mechanical skeleton or armature joining the transducers or transducer arrays, internal to a two-dimensional body in which the transducers or arrays are embedded, or external to such systems. An image formation system may comprise a flat video screen interposed between a subject and an observer or a flexible video screen conforming to an outer surface of a subject, the screens employed in conjunction with a pair of goggles utilizing synchronized stereoscopic shutters. A self-contained pair of stereoscopic imaging goggles may also be utilized. The image formation system also comprises means to determine a position of a screen with respect to a subject and an observer where a screen is utilized, and an observer and a subject where a screen is not utilized. A common feature of imaging systems in accordance with the present invention is an ability to simulate a direct natural viewing of internal features of a subject.

35 Claims, 16 Drawing Sheets

U.S. PATENT DOCUMENTS

| | | |
|---|---|---|
| 5,871,446 A | 2/1999 | Wilk |
| 5,876,342 A * | 3/1999 | Chen et al. .................. 600/443 |
| 5,984,882 A | 11/1999 | Rosenschein et al. |
| 6,023,632 A | 2/2000 | Wilk |
| 6,042,546 A | 3/2000 | Bae |
| 6,059,727 A | 5/2000 | Fowlkes et al. |
| 6,106,463 A | 8/2000 | Wilk |

\* cited by examiner

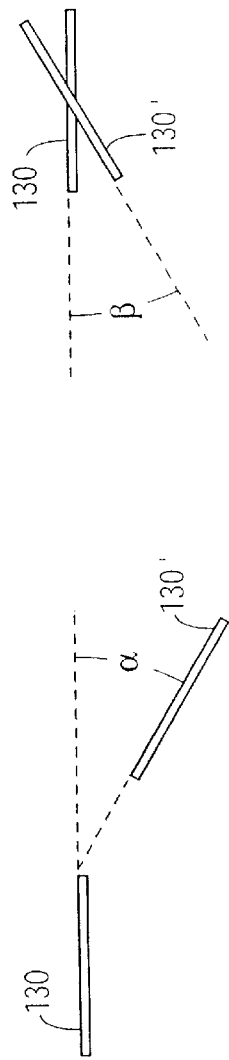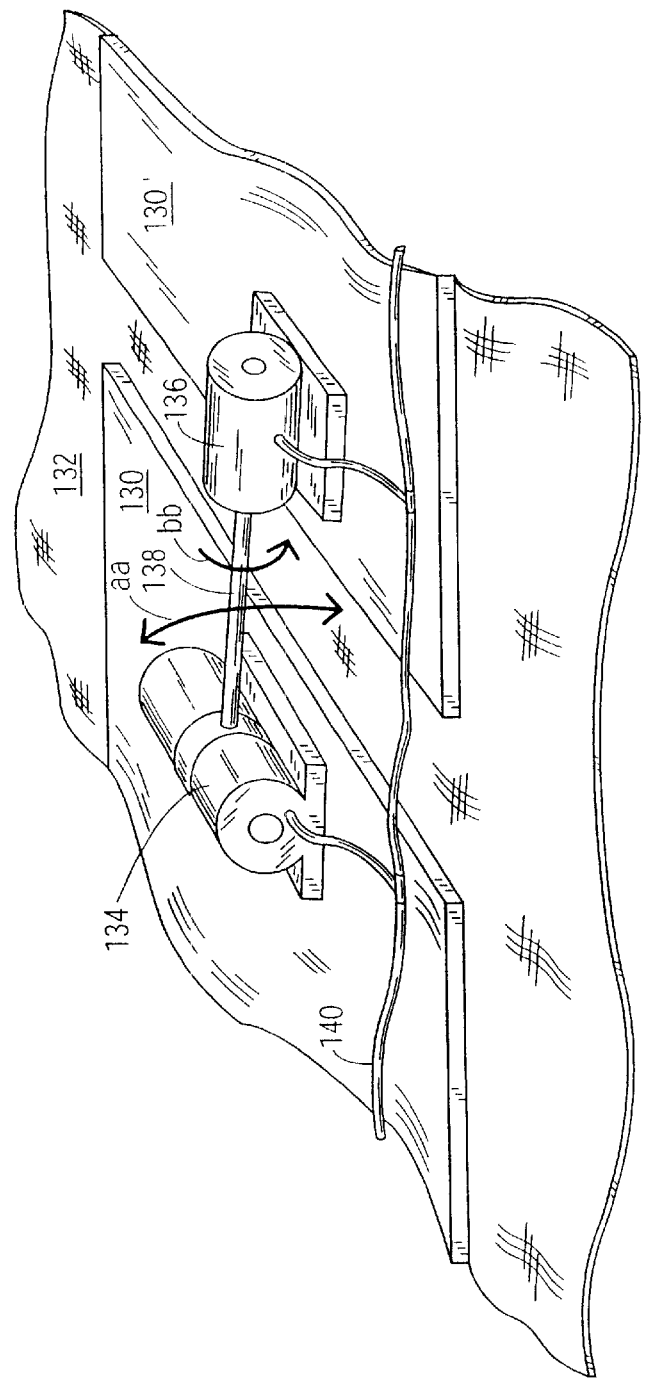
FIG. 5C
FIG. 5B
FIG. 5A

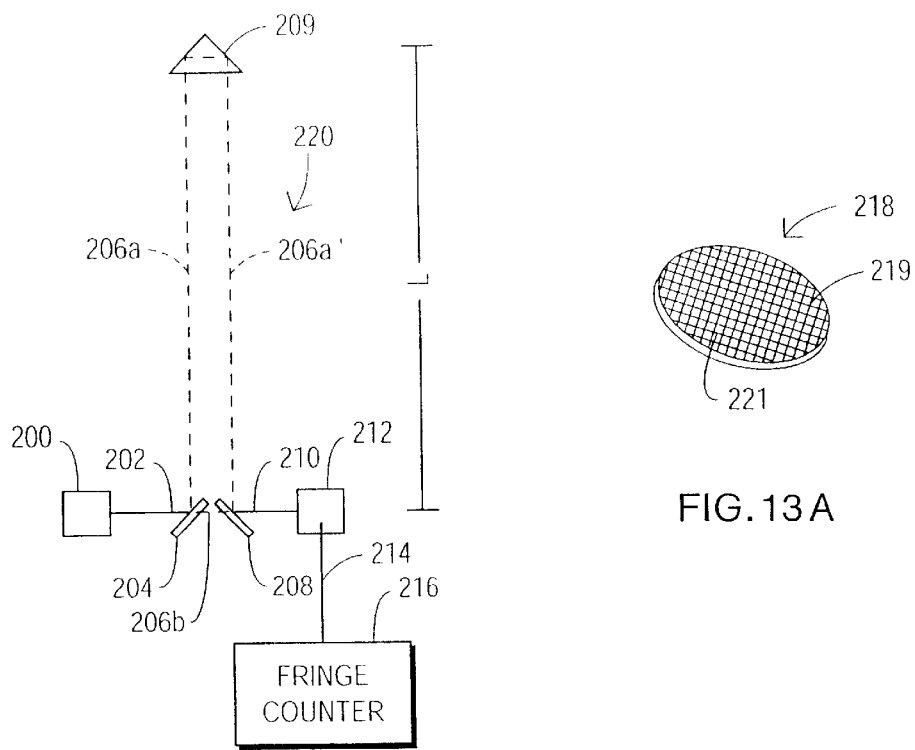
FIG. 13
FIG. 13 A
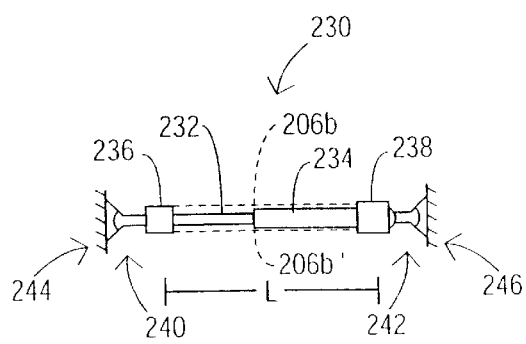
FIG. 14
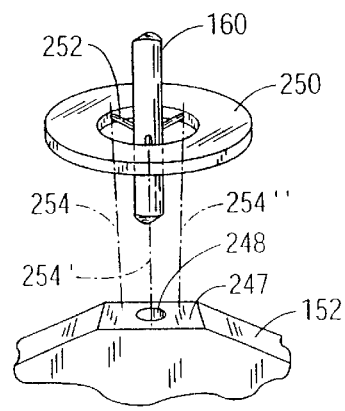
FIG. 15

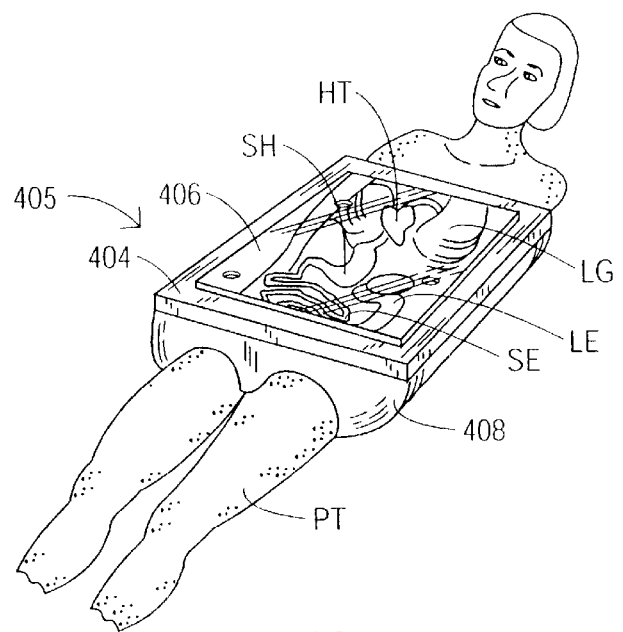
FIG. 18
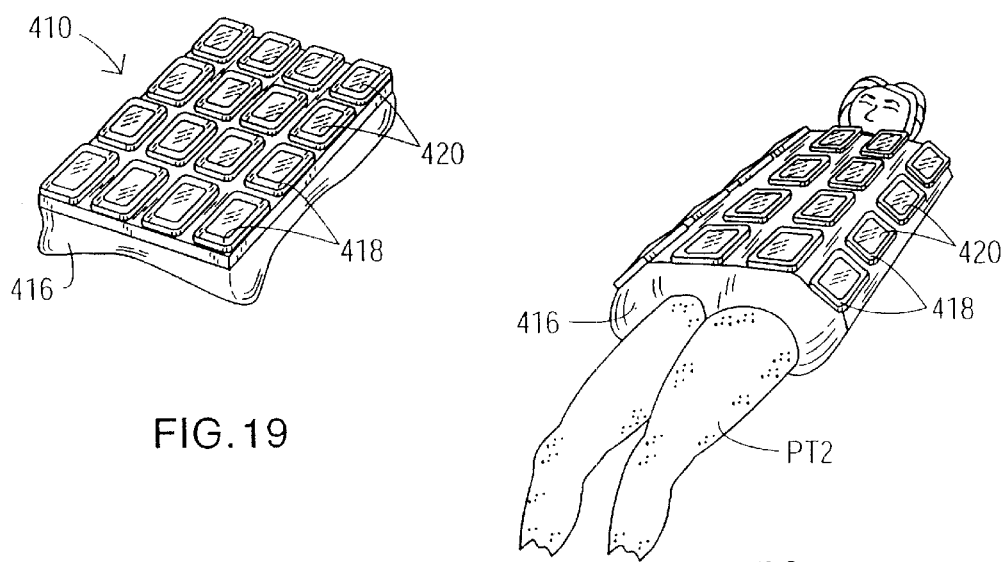
FIG. 19
FIG. 20

ULTRASONIC IMAGING SYSTEM AND ASSOCIATED METHOD

BACKGROUND OF THE INVENTION

This invention relates to an imaging system, more particularly to an ultrasonic imaging system. The invention has preferred application in the field of medical diagnosis and treatment. The invention also relates to an associated method.

An ideal medical imaging device would be compact, inexpensive, non-invasive, high resolution, and easily controlled by a physician in a general hospital, office or field environment. The ideal imaging device would enable a diagnostician or treating physician to in effect perform non-invasive dissection, selectively imaging internal structures, and perform minimally invasive or laparoscopic surgery with a facility and clarity as if overlying tissue had been removed.

While substantial advances have been made in recent decades over the traditional techniques of x-ray photography, existing medical image devices still fall far short of the ideal device on one or more criteria. Nuclear Magnetic Resonance and Computer Aided (X-ray) Tomography (MRI and CAT Scanners) offer high resolution and selective viewing of deeply imbedded structures, but neither technique can be reasonably described as "inexpensive", nor the associated devices as As "compact". Indeed, these devices, requiring specialized facilities and specially trained technicians for their operation as well as heavy capital investment, account for a substantial segment of the burgeoning cost of medical testing. Rather than being available for use as a tool by generalists or in a bedside or office environment, MRI and CAT scanning devices require specialists working in a special facility. The physical bulk of these machines and their monopolization of bedside real estate makes use in the operating theater impractical for the foreseeable future as well as posing logistical problems for field use, even for organizations with deep pockets. The expense of these machines limits their routine application to patients of the world's richest nations, leaving much of the world's population under served by late twentieth century medicine.

Ultrasonic imaging, relying neither on intense magnetic fields nor on penetrating ionizing radiation but instead on readily generated acoustic fields, holds greater promise as a vehicle for a portable and less resource-intensive diagnostic tool for the bulk of the world's population. The potential market for practical devices of this type is vast. Long before the resources will exist to put an MRI machine in every garage, a high-resolution ultrasonic imaging device could be placed in every doctor's office in every town, easing the unserved bulk of the world's population into care in accordance with twenty-first century medical standards. To date, ultrasound has not realized this promise. Images are relatively low-resolution, and tomographic; i.e., presenting a single slice of a target at a time. Existing devices are relatively simple in conception, displaying output on a CRT screen as a function of time and direction of return in a single azimuth from out going active pulses, and fall short of the promise of producing easily interpretable images of three dimensional structures in real time. It is desirable to produce acoustic imaging devices capable of greater spatial resolution and higher visual realism. "Visual realism" is a measure of the faithfulness to images perceivable if an observer were able to see directly inside a selectively transparent patient, realizing the fantasy of "x-ray vision"; the goal of visual realism entails high resolution, low distortion, and correct perspective. Operation of an ideal medical imaging device should also be user friendly. "User friendliness" emphasizes minimization of special interpretational and operational skills necessary to understand and manipulate device output. User friendliness encompasses intuitive control responsiveness, -including the ability to easily modify device output to focus on structural features of interest. User friendliness and visual realism may be collectively referred to as "perceptual acuity", which encompasses the ability not only to perceive but to readily manipulate high resolution images of complex structures, as if the structures were accessible to direct sight and manual manipulation. The objective is to build a medical imaging device of high perceptual acuity that is also compact, and at minimal cost.

To effectively reconstruct a three-dimensional image from a static array of acoustic sensors, the array must extend in two spatial dimension. Generally, the greater the resolution desired, the larger the array of sensors required. Higher resolution demands larger arrays. However, if a sufficiently large array of sensors is disposed in a rigid mounting the sensors will necessarily not conform to a particular human body surface: employing a filly rigid array in direct contact with a human body limits the array to dimensions over which a soft portion of the body is deformable. This dimensional restriction restricts both resolution and imaged tissue volume. Alternatively, to permit utilization of larger rigid arrays, a secondary medium with an acoustic transmissivity similar to that of the human body may be interposed in a volume between the array and a skin surface. The secondary medium becomes, for the purposes of image processing, just another volumetric region in a three-dimensional model. Interposition of a secondary medium between array and patient, however, may adversely affect ease of use of an ultrasound imaging device and in particular use of such a device in minimally invasive surgical procedures, where the volume occupied by the secondary medium must be penetrated by surgical instruments.

Deforming a small portion of a patient or extending the relatively acoustically dense region represented by a human body with a secondary medium effectively brings the patient to the sensors. A solution to some of the difficulties outlined above is to bring the sensors to the patient, i.e., to deform an acoustic array to conform to an outer surface of the patient's body. This approach permits utilization of larger array sizes without use of a secondary acoustic medium. Further difficulties are introduced, however.

To reconstruct an image from data collected via an array of acoustic sensors, it is necessary to know the geometric relation or configuration of the sensors; to reconstruct a precise and undistorted image, it is necessary to know sensor positions with precision. Furthermore, since the sensors are brought into contact with a living body which may further be undergoing a medical procedure it is necessary to measure geometric relations between sensors continuously and in real time, particularly if the imaging device is to be used to monitor an ongoing medical procedure.

It is difficult to simultaneously solve for transducer position and target structure utilizing only data received at sensors or transducers via transmission though a target region. Therefore, in order for signals associated with respective transducers to effectively cooperate in construction of an image or three-dimensional model in a system making use of transducers capable of relative movement, it is advantageous to provide an independent means of determining relative transducer positions.

Beyond transducer movement further sources of variation are present in any complex electromechanical system, and an acoustic medical imaging device is no exception. Transducers or other components may require replacement in the course of service, with original and replacement parts of only nominally identical electrical characteristics. Wiring may be replaced or reconfigured, and characteristic values of electrical components may drift with time. Therefore, in addition to having a method of determining the instantaneous configuration of an array of acoustic transducers, it is desirable to provide a method of detecting and compensating for random variations an drift in device characteristics.

A further question to be addressed in development of precise ultrasonic diagnostic tools is the form of visual and other device outputs, particularly with regard to optimizing visual realism.

In summary, difficulties to be overcome in improvement of the current ultrasonic medical imaging art include:

(i) Employment of larger arrays of acoustic sensors than currently employed, with resultant increase in image resolution and visual realism. In particular, finding a method of determining instantaneous relative positions of a deformable array of acoustic sensors in order to utilize data from such an array in image formation.

(ii) Compensating for variation and drift in components of an acoustic imaging system and an associated sensor position determination system.

(iii) Creating a user friendly display and control system of high visual realism.

OBJECTS OF THE INVENTION

An object of the invention is to provide a sonic imaging device suitable for forming images of internal structures of a human body.

A further object of the invention is to provide a sonic imaging device which is compact, portable, and easy to use.

Yet a further object of the invention is to provide a sonic imaging device which operates in real time.

Still a further object of the invention is to provide a sonic imaging device whose operation is useful during the execution of further diagnostic and therapeutic procedures.

A more particular object of the present invention is to provide a sonic imaging device with maximal visual realism and user friendliness.

A further object of the invention is to provide a medical imaging device which produces images of higher resolution than existing devices of similar size.

Yet another object of the invention is to provide a medical imaging device which is economical of manufacture in comparison to existing devices of similar resolving power.

Still a further object of the invention is to provide a method for maintaining a device meeting the other objectives in a condition of maximum accuracy.

These and other objects of the present invention will be apparent from the drawings and descriptions herein.

SUMMARY OF THE INVENTION

The present invention is directed to an imaging system, particularly useful in medical diagnoses and treatment, which utilizes mechanical pressure waves to obtain data pertaining to internal tissue and organ structures. More particularly, the present invention is directed in part to such imaging systems with (a) position determination subsystems for determining relative positions of electromechanical transducers in real time (b) hardware and associated techniques for calibrating those position determination subsystems and (c) display methods and devices for maximizing an availability of useful information to a user or operator.

In accordance with the present invention, a separate functionality or sub-system is provided for determining relative positions and orientations of the transducers to allow a unique image reconstruction. For a device monitoring a moving target operating in "real time", producing an output with a sufficiently high refresh rate and short enough lag time to simulate continuous current information to a human observer, inter-transducer geometry should be monitored with at least this good a refresh rate and lag.

It is necessary and desirable for maintenance of accurate and precise image reconstruction to have a convenient method of effecting an overall calibration of an acoustic medical image device. Ideally a calibration method should be simple and require minimal additional equipment.

An ideal form of the visual output for many purposes, and in particular for the purpose of ancillary use during a further diagnostic or therapeutic procedure, is one which interposes the visual output in a line of vision of the physician between physician and patient, in such manner that simulated images of organs and other internal structure of a patient detected via ultrasound appear perceptually in spatial locations identical to real locations of these structures with respect to an observer; as if the structures were directly visible to the unaided eye. In short, an ideal ultrasonic imaging device makes the patient appear partially transparent.

An ultrasonic medical imaging apparatus comprises a calibration system, a transducer position determination system and an image formation system. The calibration system adjusts the remaining two systems and is part of the overall medical imaging apparatus. The position determination system discretely determines positions of sensors or sensor arrays considered as rigid bodies, or continuously determines a shape of a flexible essentially two-dimensional body or mat in which the sensors or sensor arrays are embedded. The position determination system may be internal to a mechanical skeleton or armature joining the transducers or transducer arrays, internal to a two-dimensional body in which the transducers or arrays are embedded, or external to such structures. The image formation system may comprise a flat video screen interposed between a subject and an observer or a flexible video screen conforming to an outer surface of a subject. The screens are employed optionally in conjunction with a pair of goggles utilizing synchronized stereoscopic shutters. Alternatively a self-contained pair of stereoscopic imaging goggles may be utilized. In some particular embodiments of the present invention, the image formation system also comprises means to determine a position of a screen with respect to a subject and an observer where a screen is utilized, and an observer and a subject where a screen is not utilized. A common feature of imaging systems in accordance with the present invention is an ability to simulate a direct natural viewing of internal features of a subject.

Outputs of the position determination system along with transducer signal outputs serve as inputs of a computational stage of the image formation system. In one embodiment of an imaging apparatus in accordance with the present invention, a plurality of acoustic transducers are disposed in rigidly mounted subarrays, each subarray containing at least one transducer. The transducers of each subarray are respectively maintained in an effectively fixed geometric relationship by a rigid tile or mounting, while individual tiles are mounted on a common flexible substrate, by mechanical linkages, or else are completely structurally independent. Rigid mounting in general entails from zero to six rotational and translational degrees of freedom of each transducer subarray with respect to each adjacent subarray. Initial calibration of the ultrasonic medical imaging apparatus is achieved by placing the tiles or transducer subarrays in known locations around a calibrating body of predetermined structure. In one embodiment the calibrating body takes the form of a fluid filled cylinder with an internal target such as a sphere immersed in the cylinder at a pre-determined location. The position determination system is adjusted to return the known locations of tiles or transducer subarrays around the calibrating body. This adjustment is accomplished effectively by iterative setting of a plurality of correction coefficients to "zero out" position determination error, or "dial in" a correct set of positions. An effective number of compensatory adjustments or correction coefficients are also provided in association with the image formation system to dial in an accurate and undistorted representation of the cylinder with an image of the internal target at the pre-determined location. Drifting or uncertain parameters and in particular varying electrical component characteristics and timing uncertainties are thereby effectively compensated without individual determination of the parameters, a process similar to adjustment of a CRT image via a small number of controls.

Calibration ideally is undertaken according to a schedule based on a planned maintenance system in accordance with well-known preventative and corrective maintenance principles; comprising a periodic schedule, a use-based schedule, and an ad-hoc basis responding to replacement of failed system components. Calibration compensates for variations both in the image formation system and the position determination sub-system.

A position determination system for an array of tiles mounted to a flexible substrate may be internal and/or external, or a combination thereof "Internal" means that the position determination system is substantially contained in or directly attached to a flexible tile substrate or web to which transducers or acoustic tiles are affixed, while an "external" system is one in which components not directly mounted to a flexible substrate or coupling of the tiles must cooperate in order to collect sufficient information to determine tile position. If the tiles are filly independent, not subject to any structural constraints in their positioning, then only an external position determination system is possible. One may also subdivide position determination systems into discrete and continuous systems. A "discrete" system directly determines positions and orientations of the tiles considered essentially as a lattice of rigid bodies, the shape of any intervening surface being irrelevant. A "continuous" system monitors the shape of a flexible substrate or web or possibly a patient at a dense array of points, tile position being secondarily determined via attachments to the substrate. A continuous system is based on a mathematical model of a continuous surface, a discrete system on a model incorporating a discrete array of objects.

Continuous and discrete position determination systems may be realized either internally or externally. All four variations; internal-discrete, internal-continuous, external-discrete, external-continuous; are considered as specific embodiments of the instant invention with some specific attendant advantages and disadvantages. For many applications an internal position determination system is preferred, an internal system being less restrictive of access to a patient on which transducers are disposed. External systems however may be initially simpler of implementation, and have the potential or allowing completely unfettered placement of transducers, since no web or substrate is necessary, so the transducers or tiles may be positioned in order to maximally acoustically illuminate regions of special interest. Internal position determination systems are less obstructive to a user. Internal systems may make use of digitally encoded mechanical positioners or optical or acoustic ranging signals (discrete systems), or deformation sensitive outputs (continuous systems) involving, for example, piezoelectricity. External position determination systems may make use of acoustical or optical ranging signals or methods for monitoring the shape of a complexly curved surface. For reasons which will become clear in what follows, a preferred embodiment utilizes a continuous internal position determination system.

Between a pair of rigid objects there are in general six degrees of freedom: Three rotational and three translational. In a free-body case, considering each mounting plate or tile as the physicists' well-known rigid body, with an independent coordinate system affixed thereto, we require six parameters to fully specify the position and orientation of a second rigid body with respect to that coordinate system. However a full six degrees of freedom of motion between adjacent plates or tiles in an acoustic imaging system are not always necessary nor desirable: Distance between the plates may in general be conveniently held fixed, either absolutely or in a arcuate sense in a deformable surface, eliminating two degrees of freedom. Rotation about an axis perpendicular to a major flat surface of the tile is generally of no importance in conformation to a body surface, eliminating a third degree of freedom. Envisaging a row of plates having centers disposed along a line or arc disposed in a flexible substratum, it would in general be advantageous to allow one degree of freedom for depressing or elevating this arc and two for rotating a plate about the centers, although less freedom will suffice for many applications.

Mechanical linkages between adjacent tiles generally have an effect of reducing degrees of positional freedom. For example, a simple hinge between two bodies reduces the degrees of freedom from six to one—the hinge angle. However, the degrees of freedom cannot be mechanically reduced indiscriminately, but must be downsized in some coordinated fashion. If every adjacent pair of tiles were joined by a hinge, for example, the resulting structure would be able to bend only in one of two orthogonal axes at a time, hence unable to conform to a multiply curved surface. A related consideration to the number of mechanically allowed degrees of freedom is choosing parameters to be measured to fix a configuration of an array of rigid bodies. It is not necessary to know six parameters between every pair of bodies for this purpose. In the case that mechanical connections exist reducing the overall freedom of movement between adjacent bodies relative to the free body case, the questions of which degrees of freedom to mechanically eliminate and which degrees of freedom to measure become largely the same question. Illustrating the principle that getting an optimal answer often depends on asking an optimal question, the present invention answers these questions simply in the case of a partially rigid mechanical frame still possessing sufficient flexibility to wrap around an exterior surface of a patient.

A partially rigid mechanical frame may be combined with a method of directly encoding frame angles as outputs, a so-called digital encoding, thereby determining relative sensor positions. Limitations exist on the angular resolution of such a mechanical system, and accuracy is subject to degradation through accumulating wear. Nonetheless, such a system is conceptually simple and has the potential of being physically robust. A mechanically based system is suitable for applications where the highest attainable positional precision is not a requirement.

In an alternative to a purely mechanical system, a mechanically linked frame has a non-mechanical or optical means of position determination. In particular a mechanical frame is provided with laser interferometric rangefinders. Laser interferometry is advantageously combined with partially rigid frames, since such frames permit distance measurement to be accomplished along lines of sight determined by telescoping frame members instead of requiring tracking of completely independently moving bodies. Variable frame angles may be determined by appropriately chosen distance measurements. A variety of laser interferometric techniques, including use of optical sensor arrays containing integrated chip-level logic for pre-processing of pixel-by-pixel optical data in fringe protection, are discussed in the sequel.

A laser interferometric position determination system is relatively expensive, but has the potential of great accuracy and precision and is desirable where the highest attainable absolute positional precision is a requirement, as for example when acoustic imaging is combined with therapies involving the focusing of destructive energy on tumors. A simple yet useful combination of a partially rigid mechanical frame with determination of a small number of geometric parameters occurs in an embodiment comprising a pair of subarrays separated by a frame encompassing 0, 1 or 2 degrees of freedom. Used in conjunction with a pair of stereoscopic goggles, the frame, pressed against a patient, provides a direct simulation of a close-up binocular view into the patient at a point of contact; parameters like focus plane, depth of focus, and magnification being adjustable by electronic controls, the spacing and angle between adjacent transducer arrays being subject to mechanical adjustment. In case of 0 degrees of freedom, the device comprises a single bi-lobate array affixed to a rigid frame.

Another internal position determination system comprises an array of strain gauges distributed in a flexible substrate or web to which acoustic transducers are also attached. A pointwise determination of curvature of a surface in two orthogonal axes is equivalent to a specification of the configuration or shape of that surface, the accuracy of the specification being a function of the fineness of a grid on which curvature is determined. In practice, for a substrate of substantial rigidity but still sufficiently flexible to allow conformation to an external surface of a patient's body, position determination via measurement of local average curvature on an achievably fine grid may be satisfactory for many applications. Numerous methods of measuring curvature of a substantially planar substrate via a regular two-dimensional array of devices responsive to local strain will suggest themselves to one skilled in the art. For example, a web of conductive and flexible bimetallic strips whose conductivity varies with elastic strain may be woven together to form a fabric with warp and woof, with relatively high resistance contacts at each junction of perpendicular strips. To conduct a complete strain measurement, a current is passed across each warp strip in sequence, a voltage measurement between each pair of woof strips then determining bending along a corresponding length of that warp strip. After completion of a sequence including all warp strips, currents are then passed across each woof strip in sequence, voltage measurements being taken respectively between each pair of warps strips. A complete scan then repeats. This scheme utilizes one set of woven lines both as sensors and leads. Another scheme might for example use a first set of lines intersecting at right angles as read-outs or lead lines, and a second set of lines composed of differing material as sensors, disposed at a 45° bias relative to the first set of lines. One sensor line is conductively affixed during manufacture across each junction of lead lines. Lead lines in this case would be disposed at higher density than sensor lines, at least three being required to read each junction, which higher density might be accomplished by provision of a two layers of lead lines in a first orientation, separated from each other by an insulating layer, and one layer of lead lines in a second orientation. More sophisticated sampling schemes may also be envisaged than simple raster scans described above, reacting to strain rate information to concentrate monitoring in regions of greatest rates of change, or where subsequent measurements would reduce positional uncertainty most efficiently.

External position determination systems rely upon means external to an array of sensors or rigid sensor-carrying tiles to determine the configuration or relative positions thereof. Such systems include external transmitters, either optical, acoustic, or radiometric, which interrogate or track targets embedded on a blanket or substrate, other (substrate) passive systems, such as projecting a pattern on the substrate for computer vision interpretation, or projection of signals from the substrate aiding in tracking of points thereon. Because external position determination systems share airspace above a patient with attending physicians, imaging device displays, and other equipment, the issue arises of access and interference. Two solutions are disclosed in accordance with the present invention: a stand-off frame and an image-freezing system.

In case of a stand-off frame, a flat screen providing high-quality acoustic images is disposed at a small distance from a surface of a patient, for example, an abdominal surface, the screen being mounted on a movable arm, or space frame partially enclosing the patient. Position determination means are disposed to utilize a gap between the screen and the patient, so as not to interfere with observation of internal structures of the patient on the screen. Laparoscopic instruments and other devices may be inserted into or attached to the patient behind and or laterally of the screen. Position determination means may take the form of optical or acoustic ranging devices. Alternatively, in another feature of the present invention, a grid is projected onto on a surface of a flexible substrate or a skin surface of the patient by, for example, laser scanning. One or more digital photochips records or charge coupled devices (CCD's) record an image of this grid, computer programs known in the art calculating a three-dimensional shape of a deformed two-dimensional surface by means of two dimensional shapes of laser scanned lines recorded on the digital photochip(s). The latter method may also be utilized in the case of a flexible video-screen disposed directly on the patient, as disclosed in published International Application No. PCT/US9,808,177, publication No. WO98/47,428. In this case a laser scanner and CCD are mounted in a position above the patient so as to not interfere with operating personnel in a normal range of operating positions. In the event of moderate loss of a digital image of laser scanned lines, a processing system establishes a current position of the surface by extrapolation. In the event of severe image loss, an alarm will sound, alerting attending personnel to stand back from the patient to allow recovery of the digital image. Alternatively, if an attendant wishes to deliberately bend over the patient he or she may push a "freeze" button, which will digitally freeze the acoustically derived image on the video screen(s). A message or other indication on the video screen and/or a special tone may indicate to attending personnel that the image is now frozen. In accordance with another feature of the present invention discussed below, an observer bending over the patient, or in general changing his or her position with respect to the patient, may expect to see a faithful image of selected internal features of the patient with respect to his current viewpoint.

BRIEF DESCRIPTION OF THE DRAWINGS

FIG. 5A is a schematic perspective view of a mechanical linkage and encoding device utilizable as a sensor position determination system in an acoustic imaging device in accordance with the present invention.

FIG. 5B is a diagram showing a first definition of an angle with respect to the linkage of FIG. 5A.

FIG. 5C is a detail showing a second definition of an angle with respect to the linkage of FIG. 5A.

FIG. 13 is partially a schematic and partially a block functional diagram illustrating a laser interferometer utilizable as a sensor position determination system in an acoustic imaging device in accordance with the present invention.

FIG. 13A is a schematic perspective of a chip-level logic sensor/fringe-counter.

FIG. 14 is a detail of a single mechanical linkage equivalent to those of FIG. 6, showing a mode of utilizing a laser interferometer in accordance with FIG. 13.

FIG. 15 is a detail perspective view showing a single mechanical linkage modified to incorporate laser interferometry (FIG. 13).

FIG. 18 is a schematic perspective view showing another acoustic medical imaging system in accordance with the present invention.

FIG. 19 is a schematic perspective view showing another acoustic medical imaging system in accordance with the present invention.

FIG. 20 is a schematic perspective view showing a method of employment of the system of FIG. 19.

DETAILED DESCRIPTION OF THE INVENTION

Figure 1:
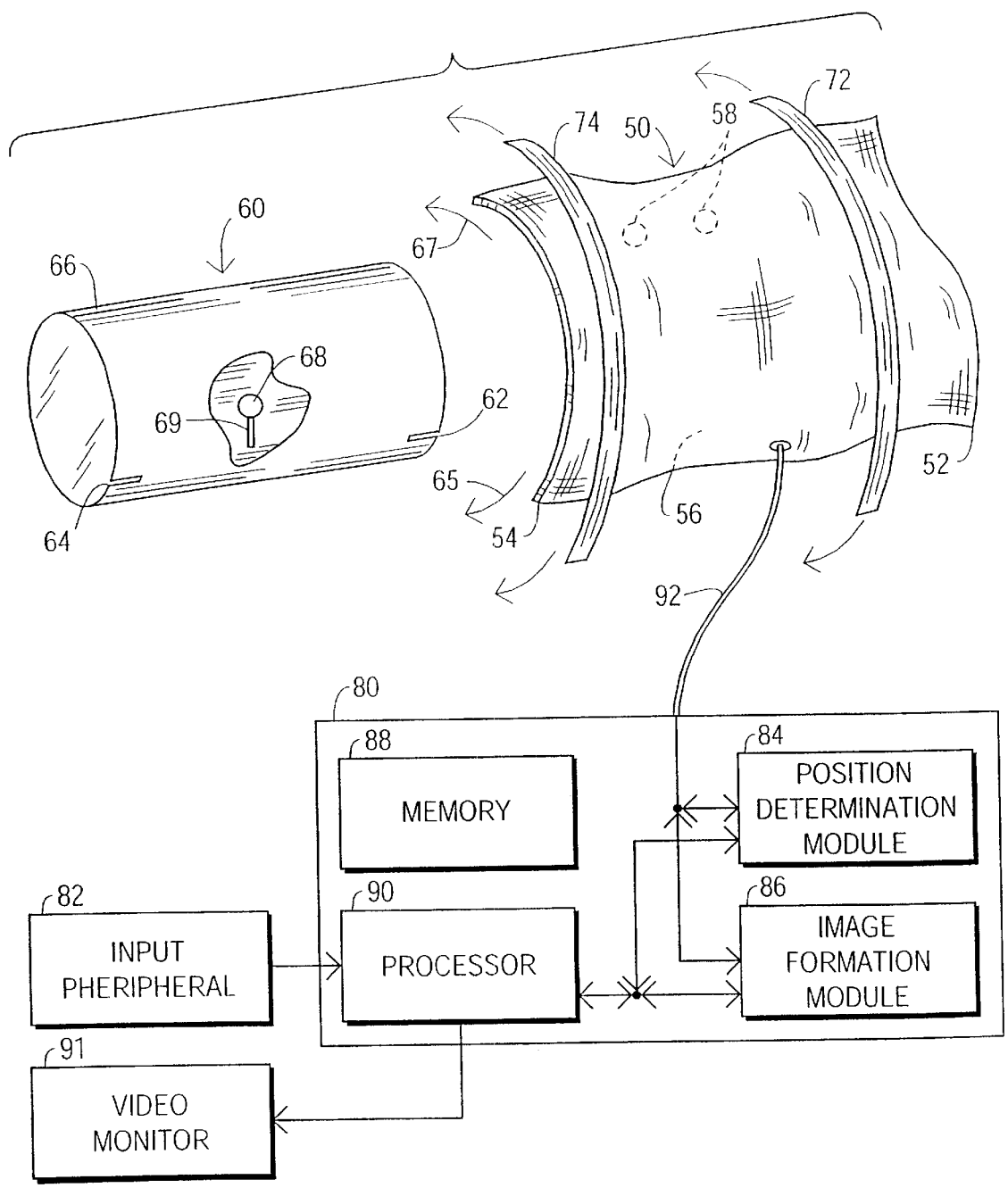
FIG. 1 is partially a perspective view and partially a functional block diagram of an acoustic imaging device and components for calibrating the device in accordance with the present invention.

A method of calibrating an medical acoustic medical imaging device in the form of a web 50 with a plurality of attached acoustic transducers 58 is outlined in FIG. 1. Transducers 50 are generally piezoelectric crystal elements capable of sonic and ultrasonic signal conversion. Flexible substrate or carrier web 50, operationally connected to a control system 80 via an umbilical 92, is wrapped around a standard calibrating body 60, in this instance a solid cylinder. Corners 52, 54 of web 50 are aligned with fiducial marks 62, 64 respectively and the web is pulled taut so that an inner surface 56 of the web is disposed securely in contact with an outer shell 66 of cylinder 60, an operation suggested by solid arrows 65 and 67. Active faces of transducers 58 are disposed on inner surface 56. Cylinder 60 contains a fluid (not designated), such as water, possessing adequate acoustic transmissibility for a range of frequencies utilized by the medical imaging device. Cylinder 60 also contains a target body 68 of known dimensions and shape mounted on a support 69 in a pre-determined location. The target body thereby has a fixed geometric relation to the fiducial marks 52, 54. Web 50 may be secured around cylinder 60 by mechanical fasteners integral to the cylinder and web (not illustrated) or by straps 72, 74. A calibration operation begins by executing a command delivered via an input peripheral 82 to control system 80. A selection of a calibrating body from among several standard bodies may also be fed to control system 80 by an operator via input peripheral 82. Standard calibrating bodies vary in geometry of the shell, geometry of the internal target, and identity of the fluid. Information concerning standard calibrating bodies may be stored in a memory 88 and automatically accessed during a calibration procedure following input of body selection by an operator. While a simple cylinder containing a single internal target is adequate for routine system calibration, more complex calibrating bodies or a series thereof may be utilized in factory calibration or following major maintenance.

Figure 2A:
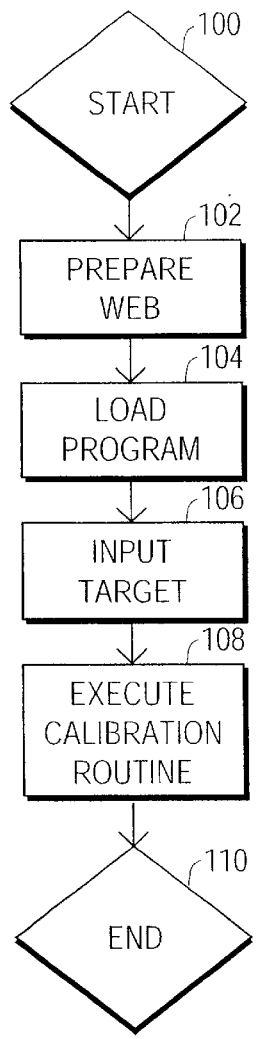
FIG. 2A is a flow chart of a method for calibrating an acoustic imaging device in accordance with the present invention, depicting operator steps.
Figure 2B:
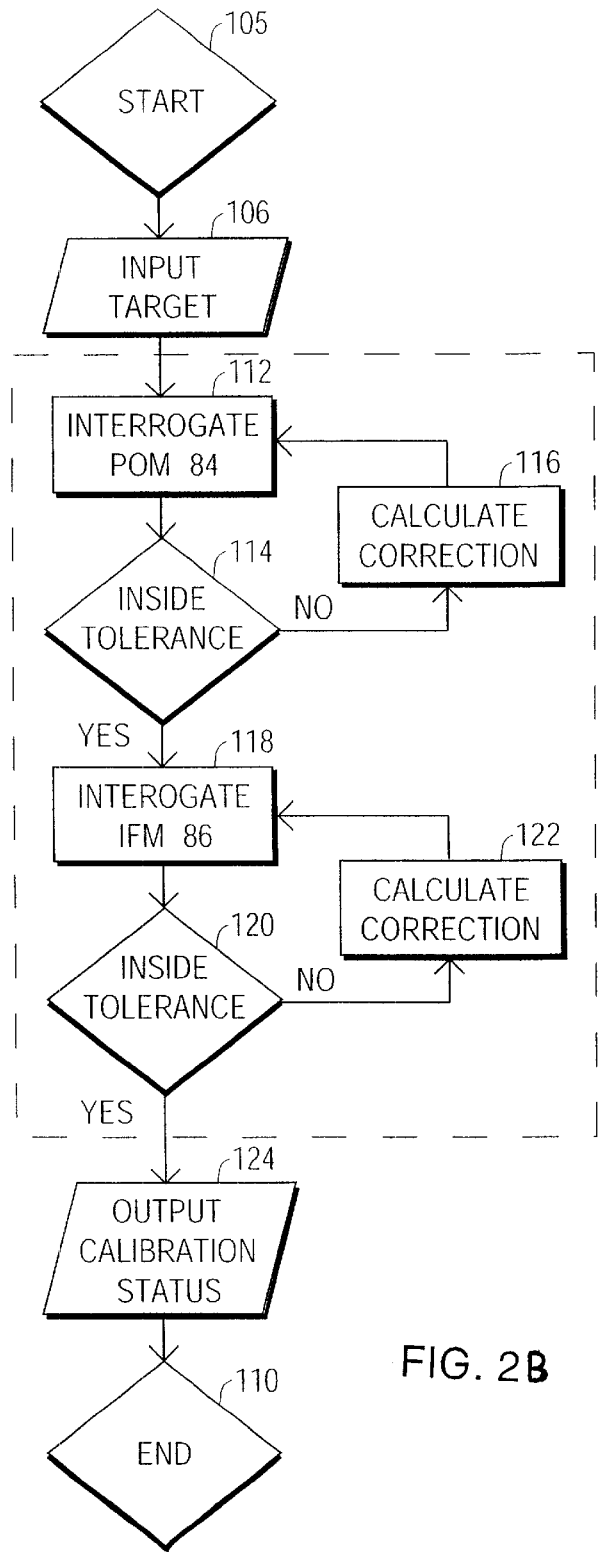
FIG. 2B is a flow chart of a method for calibrating an acoustic imaging device in accordance with the present invention, depicting machine steps.

Memory 88 also contains in a machine readable format at least one calibration program for execution by a processor 90 of control system 80. A flowchart of operator executed steps in a calibration procedure is shown in FIG. 2A, and a flowchart of machine executed steps in the calibration procedure is shown in FIG. 2B. In an overall operator executed process, (FIG. 2A) a logical start 100 is followed by mounting of web 50 on calibrating body 60 in step 102. In step 104 a calibration program located in memory 88 is loaded into processor 90 and begins execution. The operator is prompted to input the standard target body selected from a list of standard target bodies in step 106, following which input a machine calibration routine 108 is executed by processor 90 in cooperation with Position Determination Module (PDM) 84 and Image Formation Module (IFM) 86. Completion of the overall procedure is denoted by logical end step 110. The calibration routine of step 108 is shown in greater detail in FIG. 2B.

Following a logical start 105 the program commences execution by prompting a user for input in step 106. After a user response in step 106 program execution continues in step or subroutine 112 which includes an interrogation of position determination module (PDM) 84. The PDM returns putative positions of transducers 58 attached to web 50, based on outputs of position determination means to be described hereafter. Following completion of step or subroutine 112, a comparison step or test 114 determines whether putative positions of transducers 58 are within a preestablished tolerance of transducer reference positions associated with the standard calibrating body downloaded from storage means 88. In case the putative positions are out of tolerance, one or more corrective coefficients or settings are generated by processor 90 in a step 116, and used as an input to the PDM in a subsequent iteration of step 112. Steps 112, 114, 116 are repeated sequentially until a satisfactory result or exit status of test 114. Following a satisfactory exit status of test 114, program execution continues in a subroutine or step 118 which includes an interrogation of image formation module (IFM) 86. The IFM returns a putative geometry or model of target body 68, including a relation to outer shell 66 of standard calibrating body 60. Following completion of step or subroutine 118, a comparison step or test 120 determines whether putative geometry of target 68 is within a preestablished tolerance of a target reference geometry downloaded from storage means 88. In case the putative target geometry is out of tolerance, one or more corrective coefficients or settings are generated by processor 90 in a step 122, and used as an input to the IFM in a subsequent iteration of step 118. Steps 118, 120, 122 are repeated sequentially until a satisfactory result or exit status of test 120. Following a satisfactory exit status of step 120, a calibration status is displayed to the operator in step 124, which is followed by logical end 110 to both machine executed and operator executed steps in the overall calibration procedure.

Standard calibrating bodies containing more complex internal targets (not shown) than simple sphere 68 and post 69 are used for more comprehensive adjustment and compensation in a lengthier calibration procedure.

It is to be understood that position determination module 84 and image formation module 86 may be realized by specialized electronic circuitry, or by programming of generic digital components of processor 90, or a combination of these approaches, and that corrective coefficients or settings generated by sub-procedures 112, 114 may be stored by physical means associated with modules 84, 86, such as specialized non-volatile memory registers, or generically by memory 88 which may be an internal memory area of processor 90. The above description of a calibration procedure is accordingly in no way meant to limit possible physical realizations of functional components of control system 80.

Processor 90 obtains acoustic data from transducers 58 and cooperates with position determination module 84 to generate a virtual image or electronic model of internal tissue structures of a patient on which web 50 is placed. The activation of transducers 58 to generate ultrasonic pressure waves transmitted into the patient and the receiving and processing of reflected ultrasonic pressure waves received by the transducers is described in U.S. Pat. Nos. 5,666,953 and 5,871,446, the disclosures of which are incorporated by reference herein. The instant disclosure is largely concerned with providing an ancillary position sensing and determination system for ascertaining the locations of transducers 58 relative to one another. As described in U.S. Pat. No. 5,871,446, processor 90 derives two-dimensional images from the virtual image or electronic model of the patient's internal tissue structures and transmits those images in video signal form to a video monitor 91 for display to an attending physician or other operator. Processor 90 cooperates with image formation module 86 to generate the images for display on monitor 91.

In one calibration procedure utilizing the apparatus of FIG. 1, transducers 58 are operated, after the placement of carrier web 50 onto calibration cylinder 60, to transmit ultrasonic pressure waves from the transducers into cylinder 60. Pressure waves reflected from target 68 are sensed by transducers 58 and processed by processor 90 to generate a virtual image or electronic model of target 68. Processor 90 accesses memory 88 and compares the constructed virtual image or electronic model of target 68 with an electronic duplicate thereof stored in memory 88. In response to this comparison, processor 90 cooperates with position determination module 84 to determine initial or reference positions of transducers 58 relative to one another. After this calibration procedure, carrier web or substrate 50 is removed from cylinder 60 and placed on a patient. During the transfer of web 50, position determination module 84 constantly monitors changes in positions of transducers 58 relative to one another, whereby processor 90 is apprised of the instantaneous positions of transducers 58 relative to one another. This information is used by processor 90 in generating the virtual image or electronic model of internal tissue structures of a patient on which web 50 is placed.

Figure 3:
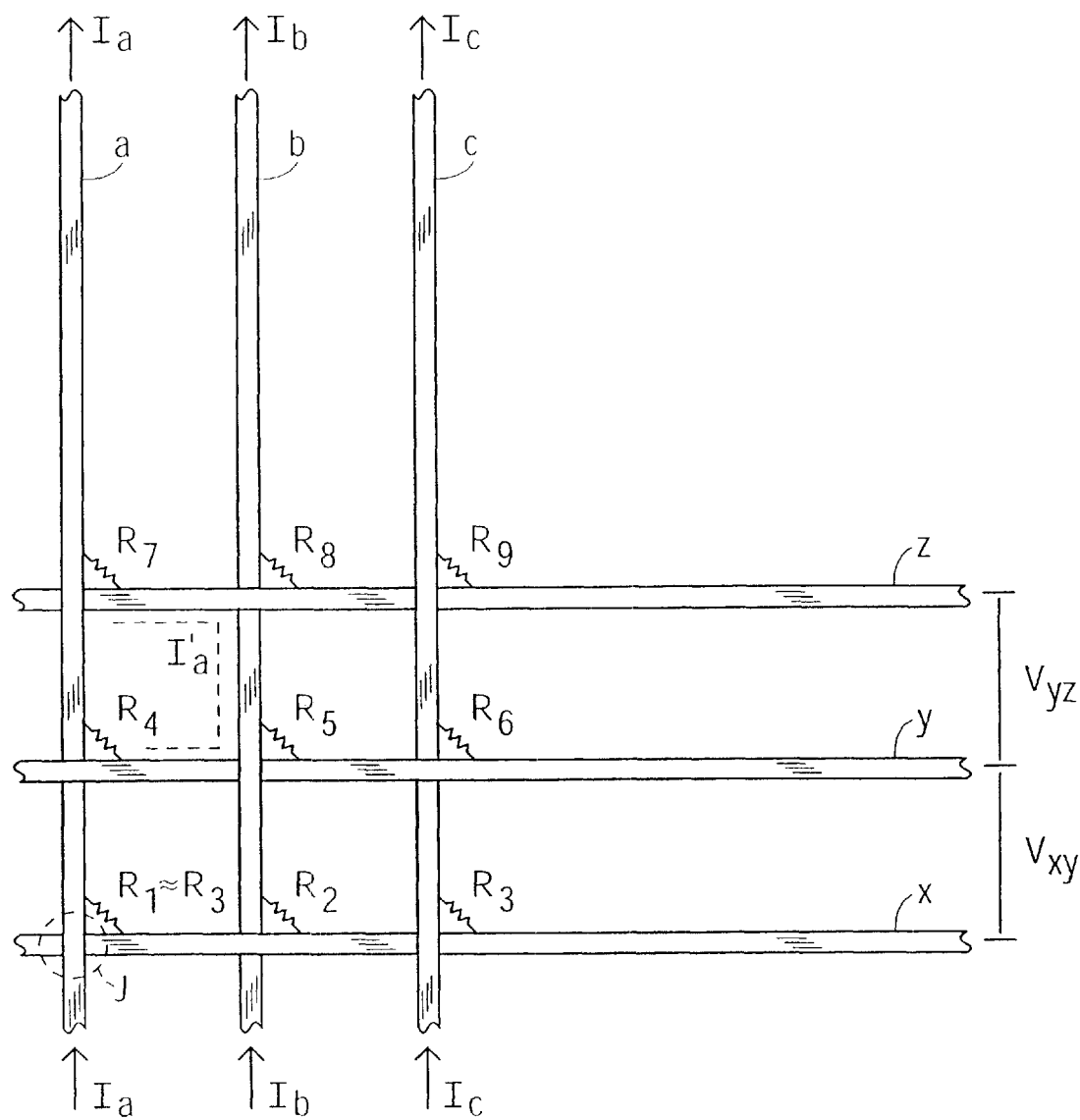
FIG. 3 is a partial schematic diagram of a system of continuous strain gauges utilizable as a sensor position determination system in an acoustic imaging device in accordance with the present invention.

A method and device for internal determination of a strain state or configuration of a web or essentially two-dimensional flexible structure is schematically represented in FIG. 3. A dense network of strain-sensitive conductive ribbons or strips is woven into the web, as shown in FIG. 3 by representative vertical ribbons or warp strips a, b, c and horizontal ribbons or woof strips x, y, z. Warp strips are generally disposed in a first orientation or parallel to a first axis, and woof strips disposed in a second orientation or parallel to a second axis. The first and second orientations are preferably substantially perpendicular to one another. Resistance per unit length of the conductive strips is a function of a local strain state and hence a local radius and sense of curvature of the strips in a plane perpendicular to the drawing. Strain sensitive resistance may be realized, for example, by deposition of a thin metallic film on a flexible plastic substrate. Adjacent warp strips and woof strips are respectively substantially electrically isolated from strips of the same orientation, and make contact with strips of the other orientation at relatively high resistance joints, represented by generic joint J with nominal resistance R; actual joint resistances are represented by $R_1$–$R_9$. In a complete determination of strain state or configuration in a flexible two-dimensional structure according to the embodiment of FIG. 3, a first series of currents $I_a, I_b, I_c, \ldots$ is passed sequentially through respective warp strips. Because of position dependent strain sensitive conductance of strip a, varying potential differences $V_{xy}$, $V_{yz}$ are realized between junctions of equidistant warp strip pairs x, y and y, z associated with passage of current $I_a$ through strip a. Nominal or design joint resistance $R_J$ is chosen sufficiently high so that alternative path current flows, represented generically by current $I_a'$, are negligible in comparison to current $I_a$. High resistance joints may be achieved for example via deposition of a thin film semi-conductor on top of a thin film conductor, by formation of a durable metallic oxide layer, or by use of a semi-conductive cement.

During current excitation of strip a by current $I_a$, potential differences $V_{xy}$, $V_{yz}$, etc. are read from terminations of the woof strips x, y, z, . . . in multiplexed blocks determined by a physical wiring configuration of the web and associated processor 90 (FIG. 1). Each strip a, b, c, . . . x, y, z, . . . must be independently addressable. Strips in a first orientation, i.e. warp strips a, b, c, . . . are current excited sequentially until exhaustion, whereupon strips in a second orientation, i.e. woof strips x, y, z, . . . are sequentially current excited. In this manner a complete strain state picture or configuration is built up, with potential difference measurements between adjacent pairs of strips in the first orientation and pairs of strips in the second orientation yielding a measure of surface curvature.

Figure 4:
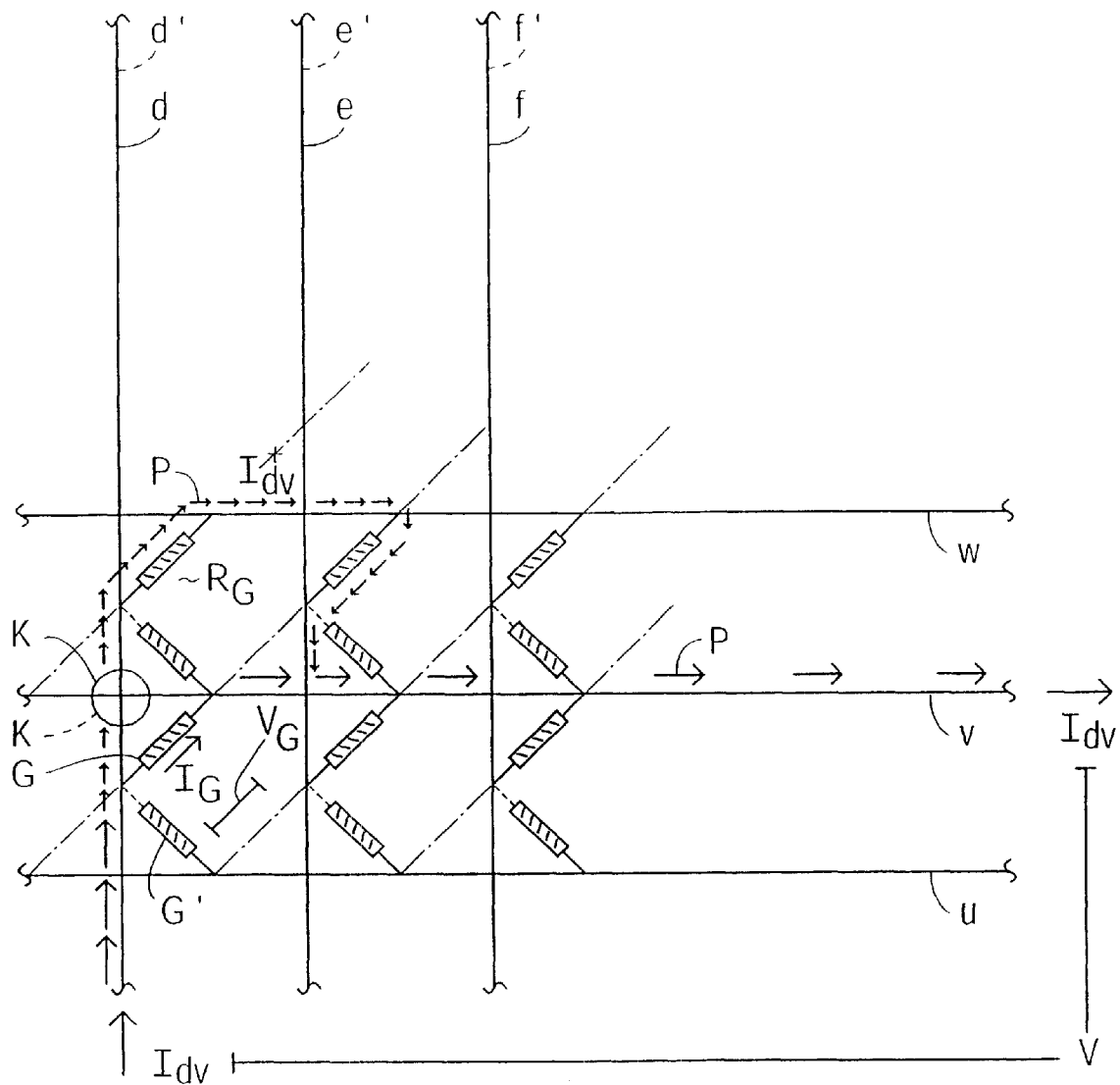
FIG. 4 is a partial circuit diagram of a second system of strain gauges in accordance with the present invention.

An alternative scheme of a continuous internal position monitoring system via strain or local curvature measurements is schematically illustrated in FIG. 4. A first set of conductors in a first orientation, represented by leads d, e, f, a further set of conductors in a second orientation, represented by leads u, v, w, in addition to a second set of conductors underlying d, e, f in the first orientation, represented by d', e', f', function only as conductive leads rather than strain gauges. A strain gauge or deformation sensitive resistive element G, G' located at each intersection K between a lead of the first orientation and a lead of the second orientation and also at each intersection K' of a lead of the second orientation and a lead of the second set of leads of the first orientation, is conductively fixed to the respective leads. Strain gauges G, G' have a nominal or design resistance $R_G$. There is no direct conductive path between leads u, v, w and d, e, f or d', e', f' at intersections K, K'. A current $I_{dv}$ passing between tennini of leads d, v, partially follows a main path P though strain gauge or deformation sensitive element G, associated with a potential difference or drop $V_G$ and a partial current $I_G$. Potential drop $V_G$ is substantially equal to a total potential drop V across the termini of leads d and v. Contributions of alternative current paths involve increasing numbers of resistive elements with an increasing remove from intersection K, as seen by a path p taken by partial current $I_{dv}*$ but are not completely negligible. The relation of potential drop V to total current $L_{dv}$ over leads d, v is thus a measure of an average local strain state in a neighborhood of element G, with a maximum weighting on element G itself. A complete strain or configuration determination involves sequentially passing total currents $I_d = I_{du} + I_{dv} + I_{dw} + \ldots$, $I_e = I_{eu} + I_{ev} + I_{ew} + \ldots$, etc. through leads d, e, . . . , d', e', . . . , clamping a single lead d, e, f, . . . of a first orientation and a block of leads u, v, w, . . . of a second orientation at a potential difference V, simultaneously measuring partial currents $I_{du}$, $I_{dv}$, . . . at leads u, v, . . . Block size is determined by a physical wiring configuration of the web and of associated processor. An increase in geometrical resolution of strain measurement may be obtained at the expense of greater processing power by employment of mathematical inversion to extract a value of $V_G$ from a complete output $I_{du}$, $I_{dv}$, $I_{dw}$, . . . , $I_{eu}$, $I_{ev}$, $I_{ew}$, . . . of a configuration determination. The form of a generic resistance as a nominal value $R_G$ plus a perturbation, along with diminishing importance of elements further removed from G in determination of $R_G$, may be exploited by those skilled in the mathematical arts to conduct the inversion with maximal computational efficiency. It is also to be understood in this embodiment that strain gauges G, G' et alia may be formed by continuously woven strips in the manner of the embodiment of FIG. 3, interwoven at a bias with respect to leads d, e, f, . . . u, v, w, . . . , it being advantageous in the case of gauges of higher intrinsic resistance to utilize a separate grid of conductive leads.

The previous two embodiments relate to a relatively dense point-to-point determination of a state of curvature or strain in a substantially two dimensional body. An alternative method of determining relative positions of multiple acoustic transducers disposed in multiple mountings measures a sufficient number of degrees of freedom between pairs of adjacent mountings considered as rigid bodies. Mechanical or other encoding means may be used to measure translation and rotation between adjacent mountings. Such a method advantageously exploits a mechanical reduction in total degrees of freedom, related above in the background exposition.

A mechanical coupling and encoding device for rigid tiles or mountings in accordance with the present invention is illustrated in FIG. 5A. Tiles 130, 130' are attached to flexible substrate 132. A mechanical measurement linkage between tiles 130, 130' comprises chiefly a first pivotal coupling 134, a second pivotal coupling 136, and a connecting rod 138. Couplings 134, 136 and rod 138 together permit a pitch or depression movement of tile and a roll or torsion movement of tile 130' with respect to tile 130, as indicated by double headed arrows aa and bb respectively. Couplings 134, 136 also include digital encoders (not shown) for producing a digital output signal representing a depression angle α (FIG. 5B) and torsion angle β (FIG. 5C), the signals being transmitted via a bus 140. In the embodiment of FIG. 5A, the mechanical linkage both constrains a number of degrees of freedom between adjacent tiles and incorporates measurement components for the remaining degrees of freedom. Other mechanical linkages enabling a larger number of degrees of freedom, up to an including a complete six degrees, may be contemplated.

Figure 6:
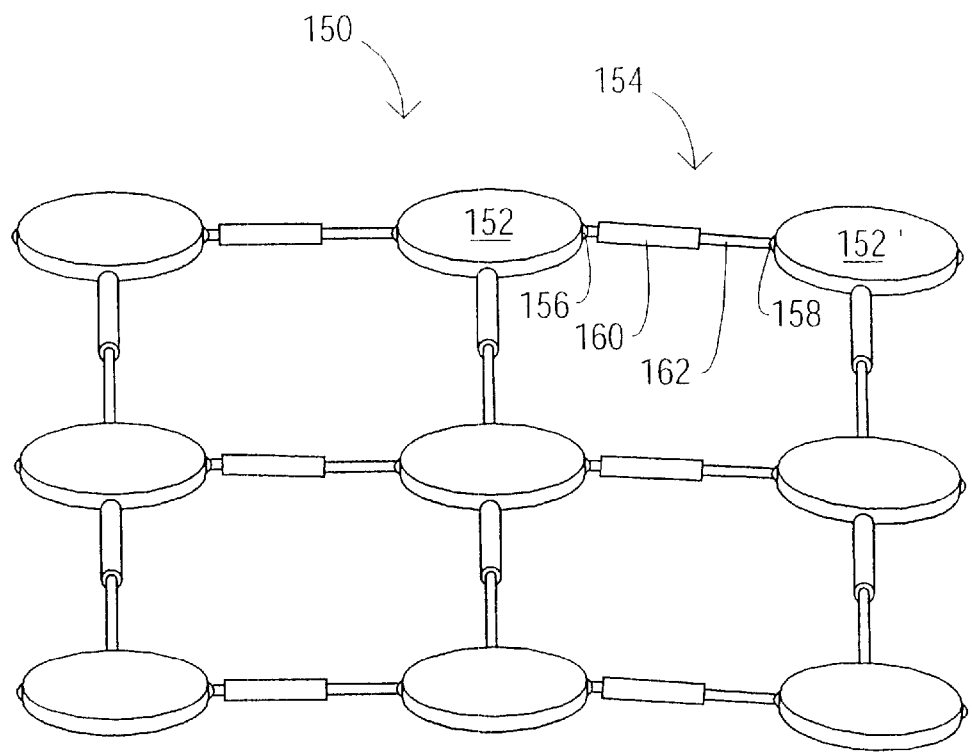
FIG. 6 is a perspective diagram of a mechanical armature utilizable as a sensor position determination system in an acoustic imaging system in accordance with the present invention.
Figure 7:
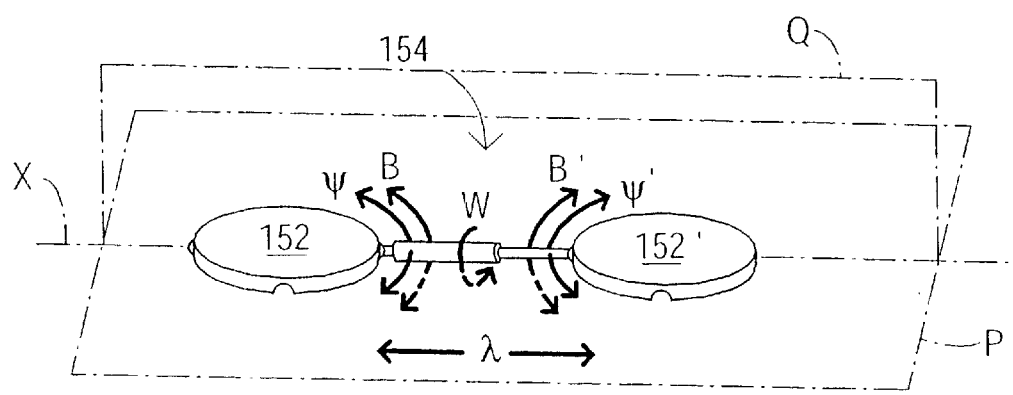
FIG. 7 is partially a perspective detail and partially a diagram showing a definition of angles in connection with a single linkage of the mechanical armature of FIG. 6.

FIG. 6 depicts a mechanical linkage measuring up to six degrees of freedom between adjacent rigid plates or tiles 152. Plates 152 are connected to each other by arms 154. A generic arm 154 comprises a piston 162 and a cylinder 160 assembled so as to allow extensible movement of piston 162 relative to cylinder 160. Ball and socket joints 156, 158 attach cylinder and piston respectively to adjacent plates 152, 152'. Realization of six degrees of freedom between adjacent plates via arm 154 is illustrated in FIG. 7. Plate 152 is free to rotate with respect to arm 154 in a substantially horizontal plane P through an angle ψ, and in a substantially vertical plane Q through an angle θ. Plate 152' is similarly free to rotate through angles ψ, θ' in planes P, Q respectively. Plates 152, 152' are also free to rotate about a major axis X or arm 154 through an angle ω. Finally, a sixth degree of freedom is realized by an extension λ of arm 154. Laser interferometric methods, discussed below with reference to FIGS. 11 and 14 may be used by those skilled in the art to measure extension, and, by selection of appropriate beam paths, rotation.

Figure 8:
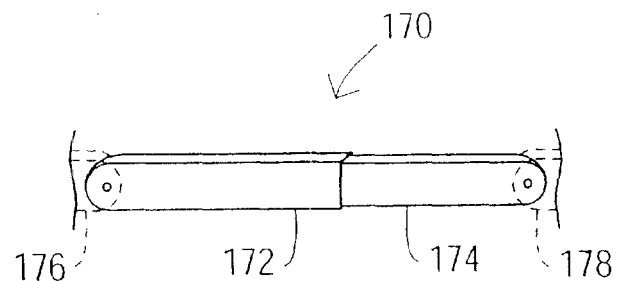
FIG. 8 is a schematic perspective view of a single linkage of a second mechanical armature utilizable in a sensor position determination system in an acoustic imaging device in accordance with the present invention.
Figure 9:
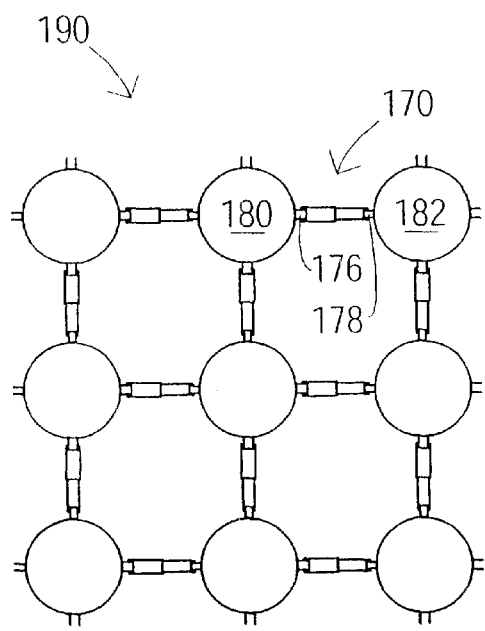
FIG. 9 is a schematic plan view of a second mechanical armature utilizing the linkage of FIG. 8.

An alternative mechanical linkage incorporating an intermediate number of degrees of freedom is illustrated in FIGS. 8 and 9. An extensible arm 170 is comprised of sliding sections 172, 174 with a substantially rectangular profile, not permitting rotation about a major axis of the arm. Arm 170 is affixed to an adjacent pair of disks or rigid mountings 180, 182, lying substantially in a horizontal plane, via brackets 176, 178 permitting rotation of the arm relative to disks 180, 182 in a substantially vertical plane. It will be perceived by a close consideration of a total assembly shown in FIG. 9 in conjunction with details of affixation shown in FIG. 8 that this alternative mechanical linkage allows at least one point on each disk 180, 182, etc. to conform to an arbitrary complexly curved surface within a range of local radii of curvature determined by dimensions of the arms and disks. An arbitrary orientation of a particular disk may not be further specified, however; though deformability of human tissue will in many cases render an orientation of individual disks or mounting determined by an overall configuration of linkage 190 adequate for acoustic coupling. Acoustic transducers (not shown) may be mounted directly on disks or plates 180. To facilitate ease of use, e.g., to prevent entanglement with other tools, a flexible web may cover the mechanical linkage of FIG. 9 excepting possibly the transducers.

Figure 10:
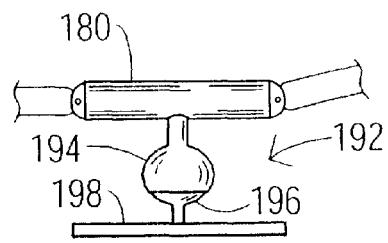
FIG. 10 is a detail elevation showing a modification of the armature of FIG. 9 for incorporation of additional mechanical degrees of freedom.

A further modification of a transducer carrier conformable to a human body, which permits a complete accommodation of an orientation of individual mounting plates to a patient or other acoustic body, is illustrated in FIG. 10. Plate 180 is affixed to a ball 196 or a socket 194 of a universal joint 192. A secondary mounting plate 198 is affixed to the socket 194 or the ball 196 of joint 192, and enjoys at least two rotational degrees of freedom relative to plate 180. Measurement of an angular position of joint 192 may again be accomplished by laser interferometric methods, which will now be discussed in detail.

A laser interferometric distance measurement device is illustrated in FIG. 13. A laser diode 200 projects a coherent monochromatic light beam 202 incident to a first beam splitter 204, where the beam is divided into partial beams 206a, 206b. Partial beam 206a is reflected by a prism 209 and returns as reflected beam 206a', which is recombined with partial beam 206b at a second beam splitter 208 to form a recombined beam 210. Beam 210 is incident on a photodetector 212, which contains a linear sensor array (not shown) for detecting an intensity of the recombined beam as varying over a range of a single dimension. The intensity of recombined beam 210 at a center of the range varies from a maximum when a path length difference between partial beams 206a, 206a' and 206b is an integral number of wavelengths to a minimum when the path length difference is a half-integral number of wavelengths. In addition, a fringe pattern, or pattern of maxima and minima, will move across the linear sensor array in either a right hand or left hand sense depending on whether a distance L between beam splitter 204 (or 208) and prism 209 is increasing or decreasing. An output of photodetector 212 is input to a fringe counter 216 via a connector 214. A logic unit (not shown) in fringe counter 216 combines a number of maxima incident on photodetector 212 with a sense of movement of the fringe pattern to track an instantaneous value of distance L, based on a increment to a preliminary value of L, $L_o$, established by some other means; for example, the calibration apparatus of FIG. 1.

Figure 13B:
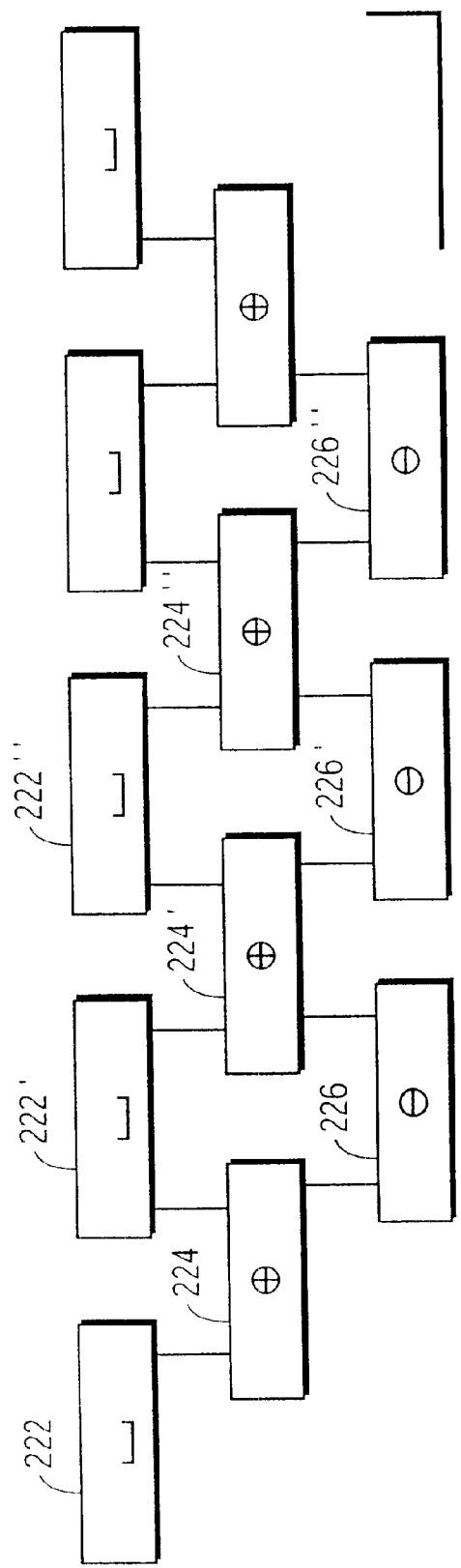
FIG. 13B is a block functional diagram of a chip-level logic optical sensor.

Overall efficiency of a fringe-counting process, as described above, may be improved by incorporating chip-level logic into a fringe-counter, or sensor array, module 216, as illustrated in FIG. 13A. In analogy with preprocessing arrangements realized in ganglia backing the human eye, a substantial amount of central pixel-level processing may be avoided in machine-vision applications by use of chip or sensor level logic. Operations like fringe or edge recognition and movement detection may be carried out by means of a small number of nearest neighbor calculations, as is illustrated schematically in FIG. 13B.

Individual pixel receptors, symbolically represented by elements 222, 222', 222" et al. are linked in nearest neighbor pairs by arithmetic units or adders 224, 224', 224". The adders are further linked by a second level of logic represented by difference modules 226, 226', 226". The calculational scheme of FIG. 13B is schematic, and is meant to exemplify a general strategy of visual data processing rather than represent a particular definite algorithm. Conceptually, a first order preprocessing layer is represented by units 222 et alia, a second order pre-processing layer by modules or units 226 et alia; third order (not shown) and higher pre-processing layers are possible. Each layer arithmetically combines and reduces data from progressively more distant neighboring pixels, and may perform such data combination at a pixel or sensor refresh rate, thereby reducing a data processing load on a central processor and allowing visual data reduction in real time. In particular, algorithmic steps in edge detection, important for fringe counting in the current application, can be front loaded. Pre-processing layers situated directly adjacent to solid state sensor elements on a physical chip level may take advantage of relatively faster analog differencing, entailing charge shifted level comparing, and a subsequent digitization step is thereby executed on a smaller, partially processed, data set.

Solid state logic for performing pre-processing calculations may either be grown in situ behind a sensor array as part of a single, monolith solid state silicon device, or alternatively, distinct integrated circuits may be "bump bonded" to form a tightly integrated whole, as shown schematically by a logic wafer 221 bonded to optical sensor array 219 in FIG. 13A.

A length measuring laser-interferometric assembly 230 is illustrated in FIG. 14. An extensible assembly comprises a pair of rigid members 232, 234 slidably coupled to one another connected via ball-and-socket joints 240, 242 to and respective transducer carriers or substrate bodies 244, 246. Electro-optical sub-units 236, 238 are mounted on members 232, 234 respectively. Subunit 236 contains diode 200 (FIG. 13) and photodetector 212, while sub-unit 238 contains prism 209. Partial beam paths 206b, 206b' pass between the subunits, and members 232, 234 serve to maintain a sufficiently straight optical path between units to insure partial beam incidence on beam splitters 204, 208 and prism 209. Assembly 230 permits a range of motion over a full six degrees of freedom between bodies 244 and 246, of which one, a length or extension L, is measured. Effectively, an extension is measured between fixed points in relation to bodies 244, 246 represented by centers of balls (not separately designated) of ball-and-socket joints 240, 246.

Figure 12:
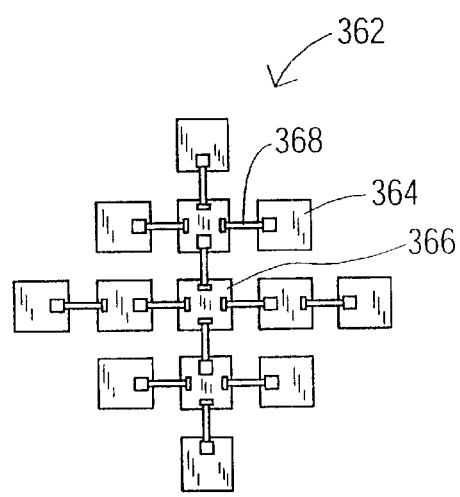
FIG. 12 is a schematic perspective view of a second mechanical armature utilizing the mechanical linkage of FIG. 5A.

A method of employment of assembly 230 to permit measurement of six degrees of freedom or possible motions between rigid bodies is illustrated in FIG. 15. A rigid body such as plate 152 of FIG. 6 is provided with a land 247. Cylinder 160 is connected to body or plate 152 via a ball-and-socket joint (not shown for clarity) at an attachment site 248. A ring 250 is rigidly affixed to cylinder 160 via rods 252 et seq. Three lines 254, 254' and 254" are conceived between ring 250 and land 247. Along each of the lines an assembly 230 (not shown for clarity) is connected between ring 250 and land 247 by ball and socket joints as illustrated in FIG. 14. The ball-and-socket joint at site 248 allows cylinder 160 three degrees of rotational freedom with respect to plate 152, identified as angles $\psi$, $\theta$, $\omega$ in FIG. 7. Three independent measures of extension along lines 254, 254', 254" suffice to fix these angles. An additional three measures of extension similarly obtained with respect to a ring affixed to piston 162 of assembly 154 determine angles $\psi'$, $\theta'$, $\omega$ of FIG. 7. A redundancy in determination of $\omega$ compensates for freedom of rotation about an axis parallel to a longitudinal axis of assembly 154 at both ball joints 156 and 158: in this arrangement piston 162 is constrained not to posses rotational freedom with respect to cylinder 160. Six measures of extension as described above thereby account for five degrees of freedom; a final repetition of the electro-optical components of assembly 230 along piston and cylinder 162, 160 itself, measuring extension $\lambda$, completes a determination of six degrees of freedom or parameters between plates 152 and 152'. It will be noted that the combined metrologic apparatus of FIGS. 7, 12 and 13 is partially self-similar, a situation necessitated by the ability of laser interferometry to determine solely extensions, and not directly angles, and the simultaneous necessity to provide a rigid extensible assembly along each measured extension to maintain a laser line-of-sight. It will be readily appreciated by those skilled in the art that a simplification of the presently described metrologic scheme may be undertaken in connection with frames or mechanical skeletons such as those represent in FIGS. 8 and 9, without departing from the spirit of the present invention, the embodiment of FIGS. 7, 12 and 13 representing a most complex case, allowing a range of fully arbitrary movement between adjacent mounting or rigid bodies.

In case of a full freedom of movement of adjacent plates 152, 152' as shown in FIGS. 6 and 7 a full two-dimensional mechanical skeleton may be executed as shown in FIG. 6 without mechanical conflict. In the case a reduced number of degrees of freedom between adjacent plates, as shown in FIG. 8, a full two-dimensional armature or skeleton may still be executed in some cases, as shown in FIG. 9, provided due consideration is given to mechanical compatibility. In general however, given a sufficiently reduced number of degrees of freedom, as shown, for example, in FIG. 5A, it will not be possible to interconnect every pair of adjacent plates and maintain flexibility in the frame. In general a tree-structure will embody the greatest degree of mechanical interconnection possible while allowing independent movement in all existing joints. Examples of such structures are shown in FIGS. 11 and 12.

Figure 11:
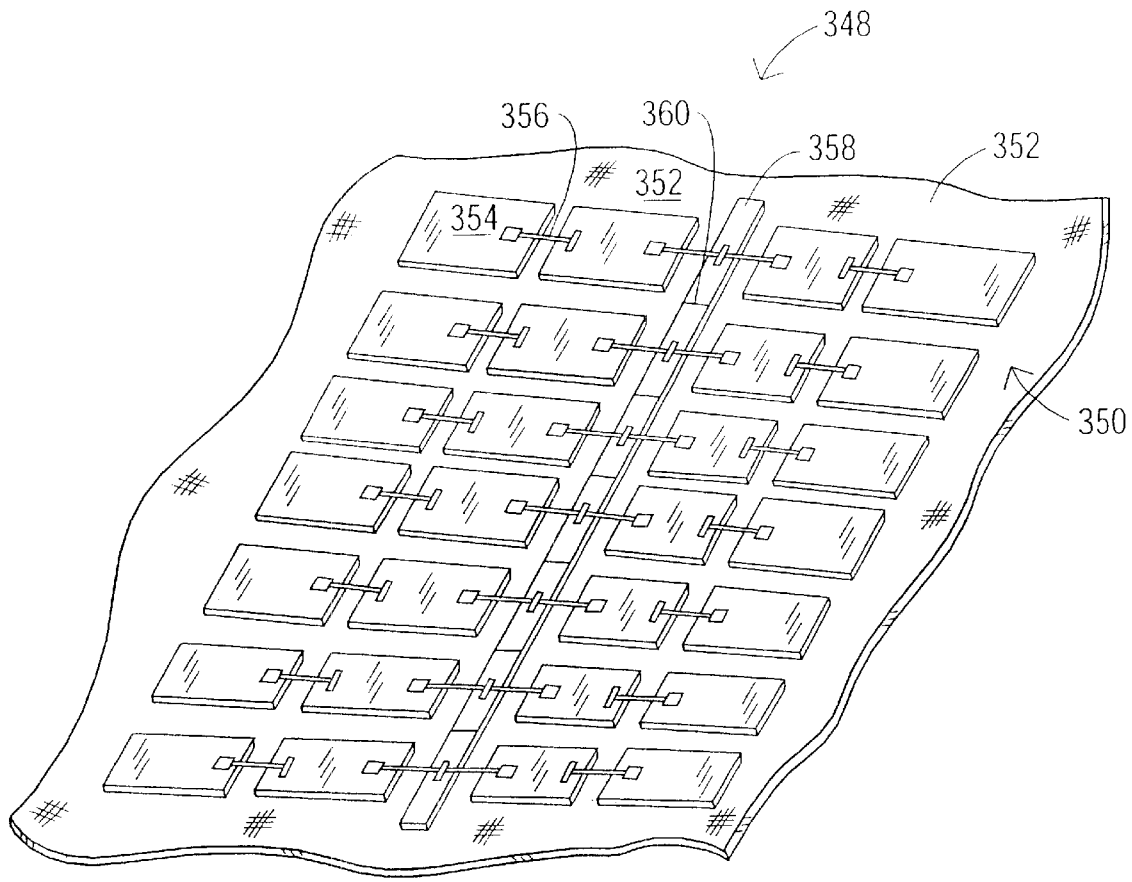
FIG. 11 is a schematic perspective view of a mechanical armature with fabric backing utilizing the linkage of FIG. 5A.

An employment of the mechanical linkage of FIG. 5A in an armature or skeleton 348 of an acoustic transducer carrier for an acoustic or ultrasonic imaging system is illustrated in FIG. 11. A flexible transducer array comprises a spine or central element 358 on which are affixed a plurality of side-arms 350. Side-arms 350 comprise one or more tiles or rigid mounting plates 354 connected by mechanical linkages 356 and forming a chain starting at the spine 358. Each linkage 356, comprising couplings 134, 136 and rod 138 of FIG. 5A, allows and encodes two degrees of mechanical freedom between adjacent tiles 354. Further hinges 360, in spine 358, each allow and encode a single degree of freedom. Armature 348 may advantageously be aligned along a dorsal or ventral axis of symmetry of a patient. The armature may also be placed around a side of a patient.

Yet another transducer-carrying armature or skeleton utilizing joints with two degrees of rotational freedom is illustrated in FIG. 12. Lacking a spine or other specialized structural element, tiles 364 connected by mechanical linkages 368 are arrayed in a symmetrical branching structure around a central tile or element 366. A symmetrical branching structure may be executed starting with any odd number of elements in a longest row, the number illustrated in FIG. 12 being "five". Such a skeleton or spider 362, realized at an appropriate scale and employing an external monitoring device (not shown), is useful for wrapping a highly curved portion of a patient's body, such as a shoulder, elbow or knee.

Lower surface of tiles 354 and spine 358 (FIG. 11) are optionally affixed a web or flexible fabric backing 352 provided with openings for acoustic transducers mounted on the under surfaces of tiles 354. Backing 352 may be redoubled to cover a top surface or tiles 354 and spine 358, completely enclosing mechanical linkages 356 and ancillary electrical wiring (not shown). It is to be understood that a mechanical skeleton as shown in FIGS. 6, 9, 11 or 12 may in general be enclosed by a flexible fabric container with side panels in the form of webs or sheets (not shown) to protect exposed mechanical and electrical linkages from damage and interference.

Figure 16:
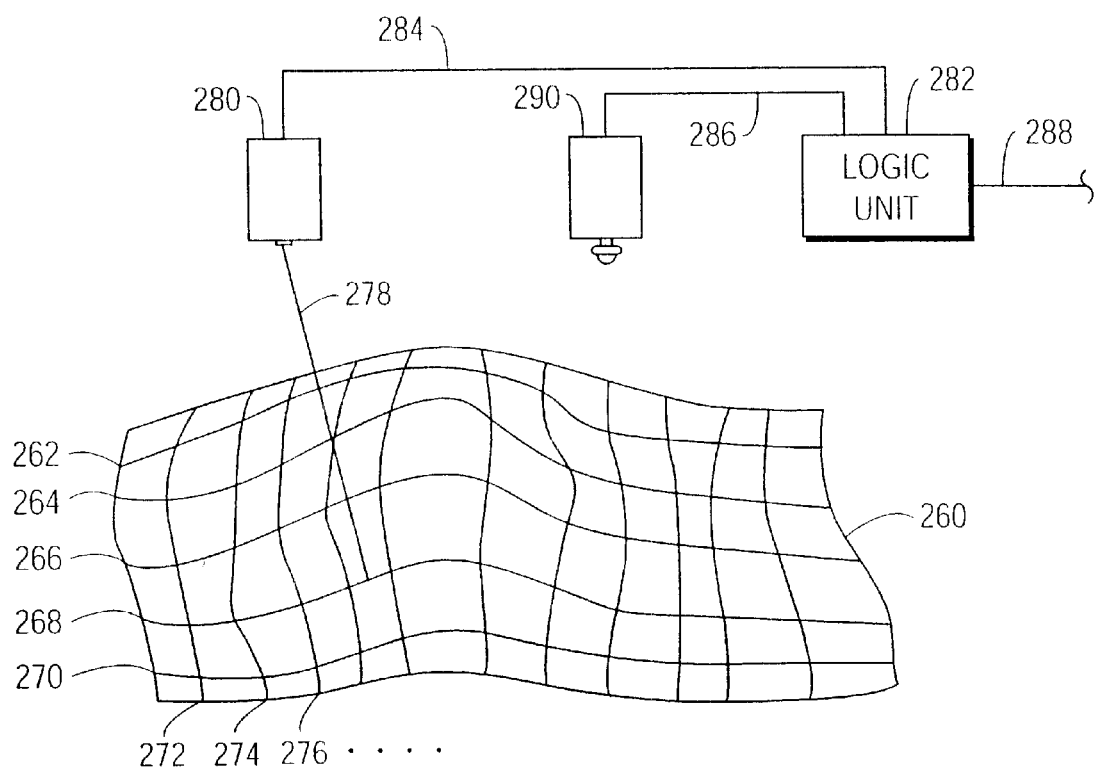
FIG. 16 is partially a schematic and partially a block functional diagram showing a system and a method of determining the shape of a surface by laser scanning.

An additional method for determining a shape of a major surface of a flexible substantially two-dimensional body, such as a web or sheet in accordance with the present invention, is illustrated in FIG. 16. A steerable switchable laser beam 278 is generated by a laser unit 280 in turn directed by a logic unit 282 via a data line 284 to scan a surface 260 in a rectangular grid pattern, represented by scan lines of a first orientation 262, 264, 266, 268, 270 and scan lines of a second orientation 272, 274, 276 etc. Because of departure from planarity by surface 260, scan lines 262 and 272 etc. in general depart from linearity, both in space and as imaged from a particular focal plane. In particular, lines 262 et alia depart from linearity as imaged in a focal plane of a digital camera 290. Unit 282 processes image data received from camera 290 via a data line 286 to deduce a shape of surface 260. Logic unit 282, digital camera 290 and laser unit 280 in this embodiment, along with associated software, comprise a particular realization of position determination module 84 of FIG. 1.

Figure 16A:
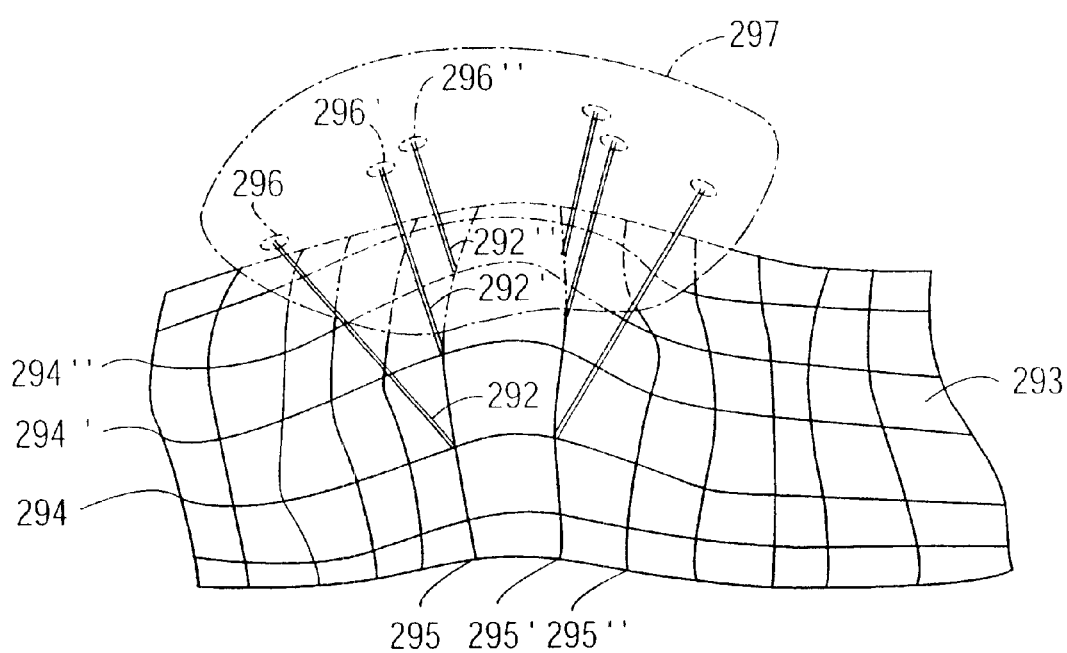
FIG. 16A is a schematic perspective view showing an alternative method of determining the shape of a surface by means of lasers.

A further method for determining a shape of a two dimensional surface via substantially normally pointing laser beams is shown in FIG. 16A. Laser beams 292, 292', 292" et al. originate from lasers (not shown) situated on intersections (not designated) of representative grid-lines 294, 294', 294" and 295, 295', 295" on a blanket or web 293. Grid lines 294, 295 et al. represent conceptual or actual structural features on web 293. The lasers are mounted in a rigid orientation, preferably normal, with respect to a surface of the web. Together with a substantial degree of rigidity of the web this rigid orientation is sufficient to establish the possibility of reconstructing a shape of web 293 from positions of spots 296, 296', 296" illuminated by the lasers on a screen 297, which screen may incorporate a fine sensor grid or photoreceptor array (not shown). Information about curvature of a surface is provided at a second overlying surface by this method much the way information about curvature of a porcupine's skin is conveyed by positions of the tips of its quills (not shown): Widely space quill tips are indicate of an underlying zone of convexity, while bunched together quill tip are indicative of an underlying concave region.

Figure 17:
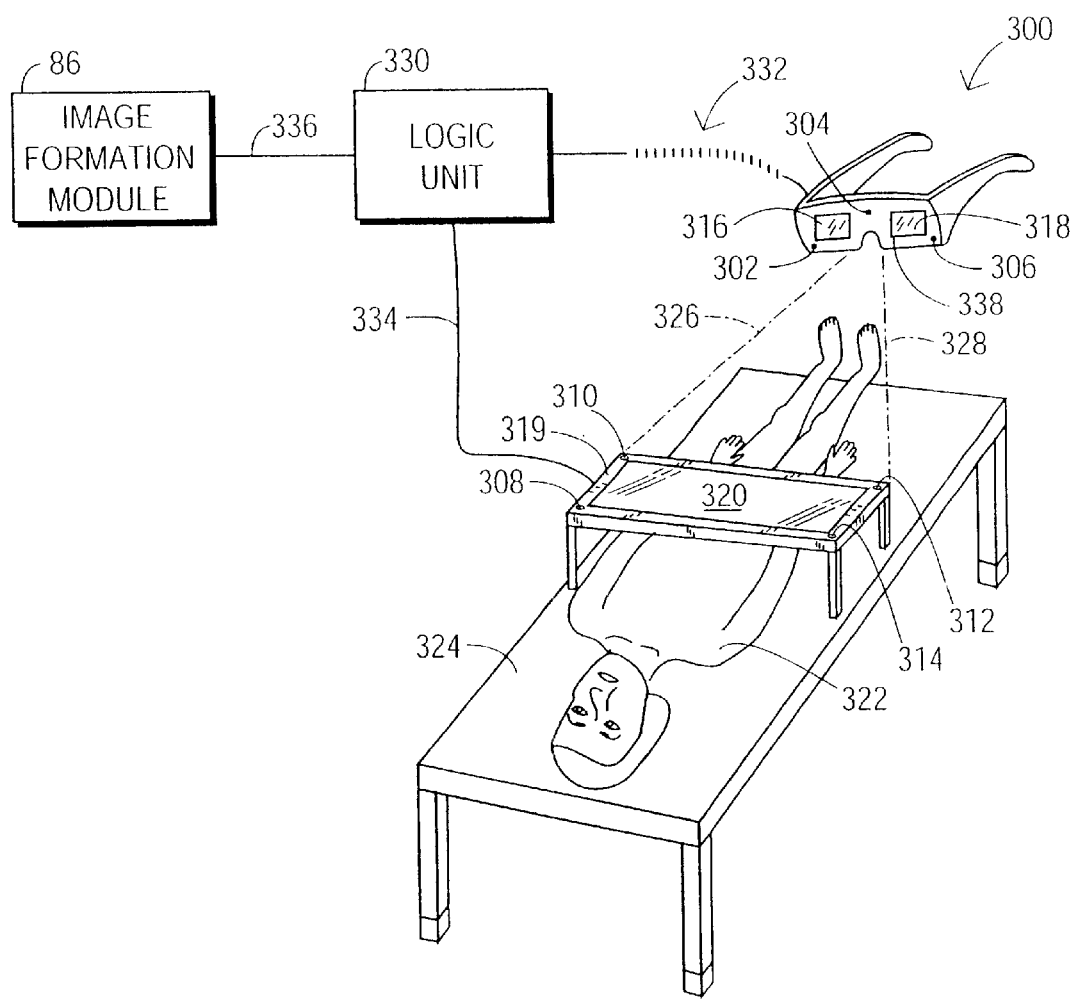
FIG. 17 is partially a schematic perspective view and partially a block functional diagram showing an acoustic medical imaging system in accordance with the present invention.

FIG. 17 illustrates an imaging system useful in medical applications. A pair of stereoscopic goggles 300 are equipped with passive position determination devices 302, 304, 306 which cooperate with active position determination devices 308, 310, 312, 314 mounted on a frame 319 of a video screen 320 in order to determine a position and orientation of a faceplate 338 of goggles 300 relative to screen 320. Raw data from position determination devices 308, 310, 312, 314 is fed to a logic unit 330 via a communication link 334. Logic unit 330 interacts with image formation module 86 (see also FIG. 1) via a communications link 336 and with goggles 300 via a communications link 332. Link 332 may be hard wired, or utilize infrared or ultrasonic signal technology to minimize encumbrance for an operator wearing goggles 300. Active position determination means 308 . . . and passive position determination means 302, 304, 306 interact via laser, infrared or ultrasonic beams, generically portrayed by beam paths 326, 328 to determine relative position and orientation of faceplate 338 via means known to those skilled in the art.

Logic unit 330 synchronizes the operation of dual electro-optical shutters 316, 318 mounted on faceplate 338 with an instantaneous image (not designated) presented on screen 320, via communication links 332 and 334. The image presented on screen 320 is derived from data data processed by module 86, in turn obtained from raw data from an ultrasonic sensor array as described elsewhere in the disclosure. A sequence of images presented in synchronization with an alternating actuation of electro-acoustic shutters 316, 318 and based on the position and orientation of faceplate 338 with respect to screen 320 creates an illusion of stereoscopic transparency of a patient 322 recumbent on an examination table 322 to an observer (not shown) wearing goggles 300.

Observer dependent stereoscopy as employed in the above described above may of course be combined with different sensing systems to provide a stereoscopic view of a patient's internal tissue and organ structures. For example, in an ultrasonic type imaging system shown in FIG. 18 which bypasses the necessity of transducer position determination, a single rigid frame 405 mounts on a reverse side an array of acoustic transducers (not shown) in contact with a flexible fluid filled sac 408 in turn place in contact with a patient PT. A flat video screen 406 is mounted on an obverse or upper side 404 of frame 405. Image production and selection is again mediated by a logic unit or processor in coordination with a position and orientation of a pair of stereoscopic goggles worn by an observer (not shown), in this case revealing organs such as the small intestine SE, stomach SH, heart HT, lung LG and large intestine LE.

In another ultrasonic imaging system which also obviates the need for determination of relative positions of individual acoustic transducers or mounting plates, an array 410 of rigid plates 418 are attached to a flexible fluid filled sac 416 and are equipped with respective flat video screens 420 and have respective ultrasonic transducer arrays operatively connected to respective image processing circuitry (not illustrated) which generate a respective array of images, associated with each plate as an individual fixed or rigid array, as shown in FIGS. 19 and 20. Passive position determination devices 302, 304, 306 (FIG. 17) are employed as before on a pari of stereoscopic goggles 300 (FIG. 17), while active position determination devices 308, 310, 312, 314 of FIG. 17 are now iterated with respect to each plate 418. A logic unit or processor (not shown) generates, partially through acoustic beam generation techniques creates as discussed above, a time series of synchronized images on each screen 420 corresponding to or depending on the instantaneous head position of an observer wearing the stereoscopic goggles. Each plate 418 and screen 420 produce an independent pseudo-stereoscopic image in response to observer head position. For viewing, the observer will naturally select screens or ports 420 closest to internal features of interest in a patient PT2.

Figure 21:
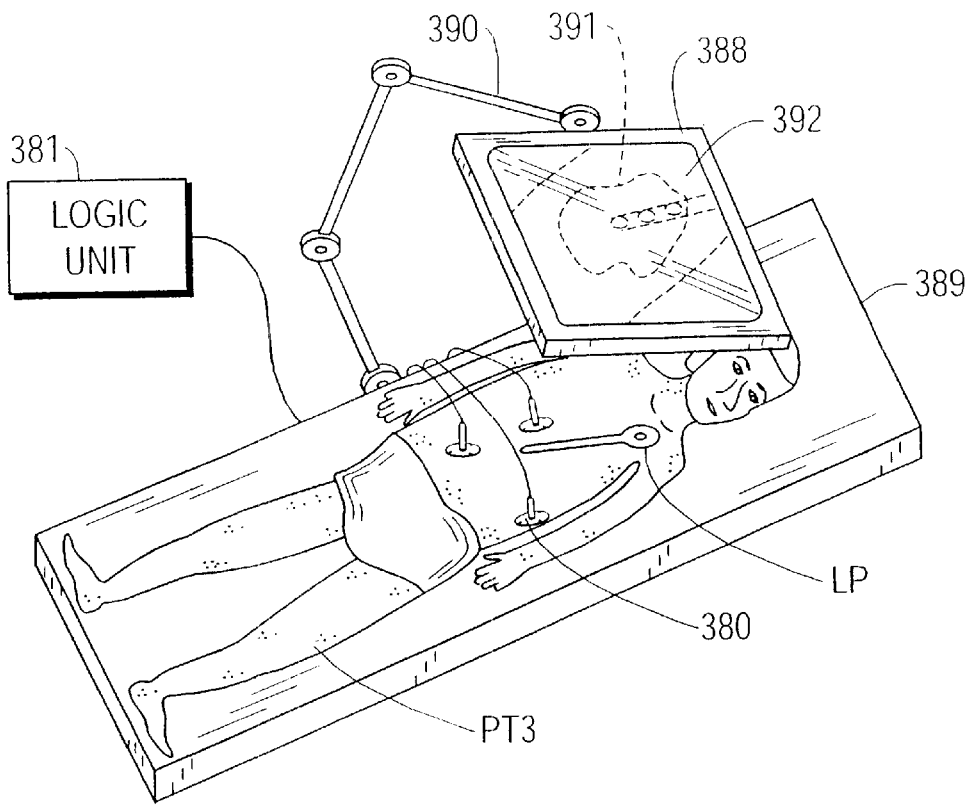
FIG. 21 is partially a schematic perspective view and partially a block functional diagram of a further acoustic medical imaging system in accordance with the present invention.
Figure 22:
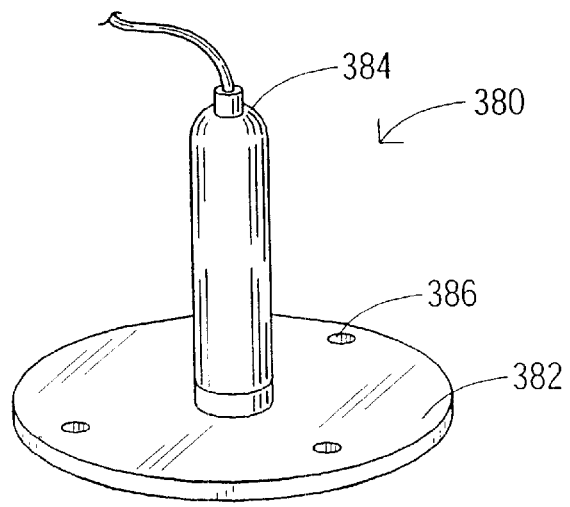
FIG. 22 is a detail schematic perspective view of a component of the acoustic medical imaging system of FIG. 21.

An additional embodiment of an acoustic medical imaging system is illustrated in FIGS. 21 and 22. As shown in FIG. 21, one or more transducer wands 380 are positioned on a patient PT3. Wands 380 are grasped by respective handles 384 (FIG. 22), manually positioned, and affixed to the patient with a mild adhesive or viscous gel. Each wand 380 includes an array of acoustic transducers (not shown) on an underside of a plate or base 382. Reflectors or markers 386 located on a top or handle side of plate 382 interact with active position determination means, such as laser or ultrasound transmitters (not shown), mounted on a reverse side of a mount 388 for a flat video screen 392. Mount 388 is attached to an examination table 389 by a multi-jointed extension arm 390, and is manually or automatically positionable over patient PT3. A logic unit or processor 381 accepting as input data from the active position determination means and from transducer wands 380 produces as output a video image 391 on screen 392. Image 391 is adapted to a relative position and orientation of wands 380 with respect to frame 388 in order to simulate a direct optical view of internal features (not designated) of patient PT3. Wands 380 are positioned as needed to allow accessing the patient by additional medical instruments and sensors, for example, a laproscopic instrument LP, and to preferentially acoustically illuminate internal features and regions of special interest. In executing image processing software, unit 381 integrates data from wands 382 to produce a single image. Regions of enhanced acoustic illumination may be indicated in image 391 by increasing focus or sharpness and by increasing brightness. The embodiment of FIGS. 21 and 22 may also be combined with stereoscopic goggles 300 FIG. 17, to produce an observer dependent stereoscopic image of internal features of patient PT3. It will be recognized that repositionable screen 392 and wands 380 are advantageous to use in the performance of other medical procedures; for example, laproscopic surgery effected by insertion of probe LP.

Other stereoscopic methods known in the art, such as viewing angle dependent screens (not shown) may be combined with the embodiments of FIGS. 17 and 21 to produce a stereoscopic viewing effect, but an effect only optimal for a preferred viewing position.

Figure 23:
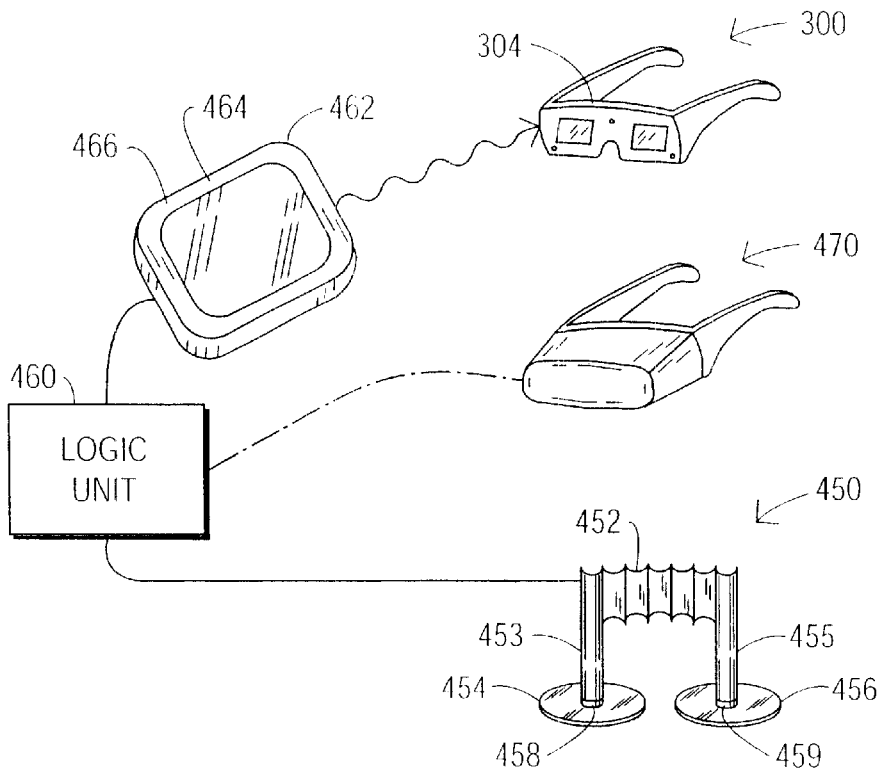
FIG. 23 is a schematic perspective view of components of yet another acoustic medical imaging system in accordance with the present invention.

Yet another embodiment of the present invention is shown in FIG. 23. A hand-held probe or scanner 450 comprises a handle 452 possessing a pair of prongs or side-posts 453, 455. A pair of plates or transducer mountings 454, 456 are attached to respective posts 453, 455 by means of a pair of joints 458, 459. Joints 458, 459 optionally allow and encode 0, 1, or 2 degrees of rotational freedom. Distal faces of plates 454, 456 are designed for pressing against an outside surface of a subject by an observer manipulating handle 452. An output of probe 450 is processed by logic unit or computer 460 to produce an image on a video display 462. In a first mode of operation, video display 462 may be observed directly in a normal video mode. In a second mode of operation, stereoscopic goggles 300 may be worn by an operator. Active display mounted and passive goggle mounted position determination components, 464 and 304, respectively, and synchronization transponder 466 control, via logic unit 460, a presentation of images on display 462 depending on a position of an operator wearing goggles 300 relative to the imaging device. In a third mode of operation a pair of wrap-around prismatic stereoscopic goggles 470 is substituted for the video display and stereoscopic goggles 300 as an output device. The image of a patient's internal organs is generated in the goggles themselves so that only the wearer of the goggles can view the image. In yet another variation of the present embodiment, goggles 470 may contain low power lasers for tracking eye-movement of an observer, and commanding an appropriate focal plane of a virtual image generated for the observer by logic unit or processor 460 and goggles 470. Thus, the image present to the user or operator is automatically varied in accordance with the direction that the user's eyes are pointed as well as the common distance focussed on by the user's eyes. Still a further variation employs a modified pair of prismatic stereoscopic goggles (not shown) with partially transparent optics, allowing a superposition of a virtual image generated by unit 460 and the modified goggles and an actual image of a the subject. In this last variation, a position determining device (not shown) between probe 450 and the modified pair of prismatic stereoscopic goggles is desirable to allow a superimposition of real and virtual images of the subject for the observer.

The embodiment portrayed in FIG. 23, in particular in the third operating mode and modifications thereof, may be reduced to a hand-held probe, a man-portable logic unit or processor and ancillary circuitry, and a head-mountable personal display device such as a pair of prismatic stereoscopic goggles; this embodiment is therefore of particular relevance to the delivery of acute medical care in difficult environments, such as wilderness and military operations areas.

In a preferred mode of operation, a medic or corpsman equipped with a back-peaceable unit would execute a preliminary examination of an injured subject or victim with aid of probe 452 and goggles 470. Optional mode switching would change between a close up or "macro" mode, and an unmagnified or ordinary mode. Macro mode permits a close inspection of features from an apparent viewpoint of direct adjacency to a skin surface, with a focus correction resulting in apparent magnification. Ordinary mode situates an observer at an apparent optical distance from a subject equivalent to a an actual distance of the observer, and permits superimposition of direct visual and acoustical images via goggles 470. In case of a device utilizing only ordinary mode a side-post 455 and transducer mounting 456 may be eliminated, leaving a probe functionally identical with wand 380 of FIG. 22. Alternatively logic unit 460 can be configured to optionally accept two or more wands in the manner of the embodiment of FIG. 21. In order to perform an emergency or battlefield medical procedure, one or more probes may be strapped on the patient or held in place by an assistant. A second pair of stereoscopic goggles may be provided to a second observer/assistant, realizing a second independent stereoscopic viewpoint, with provision of adequate processing power in unit 460.

Figure 24:
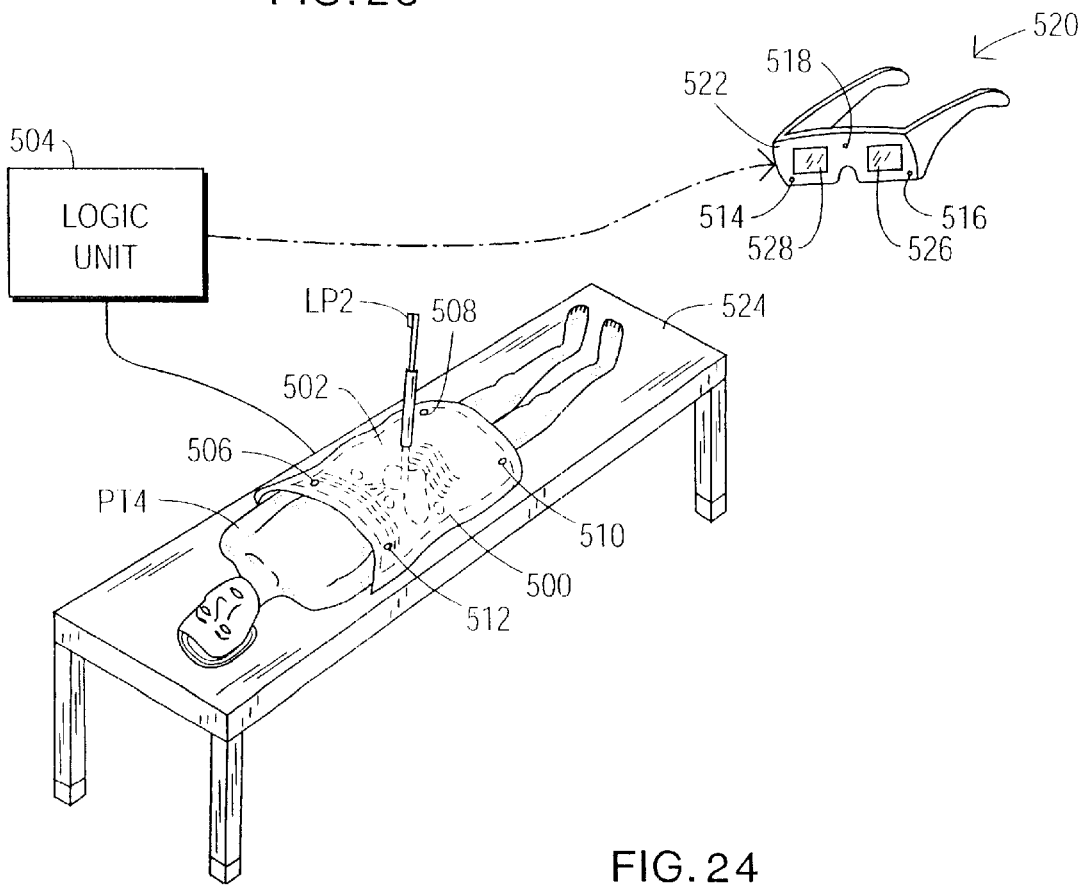
FIG. 24 is partially a schematic perspective view and partially a block functional diagram of yet a further acoustic medical imaging system in accordance with the present invention.

As shown in FIG. 24, a medical imaging system comprises a flexible substrate or web 500 carrying an array of acoustic sensors with active faces protruding from a reverse or lower side of the web (not shown). Each sensor comprises one or more acoustic transducers affixed to a rigid tile or mounting plate (not shown in FIG. 24). A continuous position determination system, such as the sensor net of FIGS. 3 or 4, is provided internal to the web 500. Alternatively the laser net projection assembly of FIG. 16 may be utilized to determine a configuration of web 500. On an obverse or upper side of the web, a flexible video screen 502 is provided. A position determination module 84 and image formation module 86 of FIG. 1 are incorporated by functionality in a logic unit or processor 504. A plurality of fixed points 506, 508, 510, 512 attached to individual transducer-carrying tiles, and hence locatable with respect to the configuration of web 500 by the position determination system, interact with fixed points 514, 516 518 affixed to a face plate 522 of observer stereoscopic goggles 520 by transmission and reception of ultrasound, infrared or laser pulses. By acceptance of a lower frame rate two observers may share the same web, each observer receiving one half of a total frame rate. Alternatively, unit 504 may be configured to devote a portion of screen 502 to each observer at full frame rate; for example, a physician and an assistant each standing on opposite sides of table 524 may see alternative interior views of a patient PT4, including, for example, distinct views of a tip of a laproscopic instrument LP2, on distinct areas of video screen 502. Receiving sensor data indicating position and orientation of an observer or observers, logic unit or processor 504 directs appropriate alternating stereoscopic views to screen 502 in synchronization with operation of electro-optical shutters 526, 528 of goggles 520.

In order to properly represent observer dependent views in real time, a web configuration and observer position must be determined in each time increment of a frame rate, for example, 30 frames per second, and an appropriate image presentation must be calculated based on output of data from sensors affixed to web 500. Determination of blanket configuration is necessary both for correct interpretation of sensor data and correct presentation of a video information on a curved screen. The entire problem involving observer position, video screen and sensor position, and appropriate image formation is interconnected, and must be solved and recalculated at a high enough frame rate to prevent unacceptable image flicker and lag. Selective defocus or focal plane choice can be achieved in response to user voice commands. Alternatively, pupil and corneal muscle movement are detectable by devices located interior to the stereoscopic goggles 520, permitting a simulation of natural ocular focusing and direction of observer attention.

Complete observer dependent real time stereoscopy of internal features of a patient, perceived in apparent real physical locations and allowing viewing from a wide choice of angles is most preferred, whether achieved through prismatic partially transmissive stereoscopic goggles 470 of FIG. 23, the flexible video screen and shutter equipped stereoscopic goggles 520 of FIG. 24, or the repositionable flat video screen 392 of FIG. 21. These embodiments, which place the heaviest demands on processing speed and software approach the ideal of a field transportable device requiring minimum ancillary equipment and allowing conceptually transparent visualization of interior structures of a patient.

In another embodiment fringe-detection signal processing may be moved off the blanket or web. Multiplexed optical transmitters or lasers are positioned in a central unit connected to a fiber optic umbilical which feeds the flexible web or blanket; multiple paths are carried on fiber with the exception of optical gaps in the vicinity of mechanical degrees of freedom. Optically transmissive fibers have substantially constant optical path length under flexure; therefore an optical path carried on fiber with exception of a gap will have variable optical path length attributable to the gap, and in the present case, permit remote reading of a variable gap size. Electrical overhead in the blanket is thereby reduced, and data reduction operations moved to a location of a central computer or processor.

By a similar method a "porcupine" embodiment may be realized with a central, multiplexed, array of laser light sources, transmitted to a web or blanket by a fiber optic tree terminating in apertures oriented normally to a local web surface, projecting beams on an external screen, as discussed above. The fiber optic/optical gap method and porcupine method may be combined utilizing a single multiplexed feed; in this case, porcupine data may serve as a supplement or gross positioning check while fringe counting data provides a fine positional calibration for the web or blanket.

One of ordinary skill in the art will appreciate that the various position determination assemblies and output modes may be modified to form further, equivalent medical imaging devices. For instance, the mechanical linkages of FIGS. 6 or 9 may be combined with the flat screen video screen of FIG. 17. All of the imaging systems disclosed may in turn employ the calibration system of FIG. 1. Accordingly, it is to be understood that the drawings and descriptions herein are proffered by way of example to facilitate comprehension of the invention and should not be construed to limit the scope thereof.

What is claimed is:

1. An imaging apparatus comprising:
   a plurality of acoustic transducers;
   position sensors different from said transducers and operatively connected to said transducers for monitoring said transducers to determine substantially instantaneous positions of said transducers relative to each other; and
   an image processor operatively connected to said transducers and to said sensors, said processor being programmed to determine three dimensional shapes of objects in response to ultrasonic echo signals received by said transducers and in accordance with the detected positions of said transducers relative to each other.

2. The imaging apparatus defined in claim 1, further comprising a plurality of substantially rigid substrates each carrying at least one of said transducers; and
   at least one flexible connection coupling said substrates to one another so that said substrates are extendible at a variable angle with respect to one another,
   said sensors being operatively connected to said substrates for monitoring said substrates to determine substantially instantaneous positions of said substrates relative to each other.

3. The imaging apparatus defined in claim 2 wherein said sensors include a plurality of interferometric metrology devices.

4. The imaging apparatus defined in claim 3 wherein said metrology devices are optical, each of said metrology devices including:
   a laser diode emitting electromagnetic energy of a predetermined frequency;
   a beam splitter, said laser diode and said beam splitter being located on a first one of said substrates;
   a reflector on a second one of said substrates; and
   a fringe counting device disposed on said first one of substrates and receiving a first beam from said splitter and a second beam reflected from said reflector.

5. The imaging apparatus defined in claim 4 wherein said processor is operatively connected to said fringe counting device for tracking the positions of said substrates relative to each other in response to changes in fringe counts.

6. The imaging apparatus defined in claim 5 wherein said substrates each carry a respective video screen, said processor being operatively connected to said video screens for providing respective video signals thereto, said video signals each encoding an image of objects located near a respective one of said substrates.

7. The imaging apparatus defined in claim 6 wherein said processor includes means for highlighting a selected feature of said objects.

8. The imaging apparatus defined in claim 2 wherein a plurality of apertures are provided in interstitial spaces between said substrates for enabling traversal of the imaging apparatus by medical instruments.

9. The imaging apparatus defined in claim 1, further comprising video display componentry operatively connected to said processor for displaying an image of said objects in response to signals from said processor.

10. The imaging apparatus defined in claim 9 wherein said processor includes software-modified generic processing circuits for generating two images of said objects from two distinct angles, and wherein said video display componentry includes hardware for presenting said two images to different eyes of a viewer so as to simulate binocular or stereoscopic vision.

11. The imaging apparatus defined in claim 1, further comprising a calibration reference body disposable in pressure-wave-transmitting contact with a substantial number of said transducers.

12. The imaging apparatus defined in claim 11 wherein said reference body includes a substantially rigid shell filled with a medium having a first velocity of ultrasonic wave propagation, said reference body further including a substantially fixed object disposed at a fixed and known location in said medium, said fixed object having a second velocity of ultrasonic wave propagation different from said first velocity of ultrasonic wave propagation.

13. The imaging apparatus defined in claim 12 wherein said shell is substantially cylindrical, said medium is a gel and said fixed object is a rigid body.

14. An imaging apparatus comprising:
   a plurality of acoustic transducers;
   a carrier supporting said transducers;
   a processor operatively connected to said transducers for determining three dimensional shapes of objects in response to ultrasonic echo signals received by said transducers;
   position determination componentry operatively connected to said processor and providing data to said processor determinative of relative positions of said transducers; and
   a calibration reference body disposable in pressure-wave-transmitting contact with a substantial number of said transducers,
   said position determination componentry including software-modified generic digital processing circuits determining initial relative positions of said transducers when said transducers are in pressure-wave-transmitting contact with said calibration reference body and further determining changes in positions of said transducers relative to one another during a transfer of said carrier and said transducers from said calibration reference body to a subject.

15. The imaging apparatus defined in claim 14 wherein said reference body includes a substantially rigid shell filled with a medium having a first velocity of ultrasonic wave propagation, said reference body further including a substantially fixed object disposed at a fixed and known location in said medium, said fixed object having a second velocity of ultrasonic wave propagation different from said first velocity of ultrasonic wave propagation.

16. The imaging apparatus defined in claim 15 wherein said shell is substantially cylindrical, said medium is a gel and said fixed object is a rigid body.

17. A method for calibrating an acoustic array, comprising:
(i) providing a calibration body of known dimensions filled with an acoustic medium and containing a calibration target of known acoustic properties at a pre-determined location inside said body;
(ii) placing an array of acoustic transducers in operative contact with an exterior surface of said body, said transducers being mechanically connected to each other via a carrier or substrate;
(iii) operating said transducers to transmit pressure waves from said transducers into said body;
(iv) receiving pressure waves reflected from said target;
(v) processing the reflected pressure waves to generate a virtual image or electronic model of said target;
(vi) automatically comparing said virtual image or electronic model of said target with a stored electronic duplicate of said target;
(vii) in response to the comparing of said virtual image or electronic model with said stored electronic duplicate, determining initial or reference positions of said transducers relative to one another;
(iv) removing said carrier or substrate from said body after the determination of the initial or reference positions of said transducers; and
(v) automatically monitoring changes in positions of said transducers relative to one another during the removing of said carrier or substrate from said body, thereby determining instantaneous positions of said transducers relative to one another.

18. The method defined in claim 17 wherein the automatic monitoring of said changes in positions includes operating position sensors separate from said transducers.

19. The method defined in claim 18 wherein said sensors include a plurality of interferometric metrology devices, the operating of said metrology devices including counting wave interference fringes.

20. The method defined in claim 19 wherein said metrology devices are optical, the operating of each of said metrology devices including:
energizing a laser diode to emit a beam of electromagnetic energy of a pre-determined frequency;
splitting said beam into a first beam component and a second beam component;
reflecting said first beam component; and
combining the reflected beam with said second beam component to generate interference fringes; and
counting said interference fringes.

21. The method defined in claim 20 wherein the monitoring of the changes in positions of said transducers includes tracking the positions of said transducers relative to each other in response to the counting of said interference fringes.

22. The method defined in claim 21, further comprising:
placing the removed carrier or substrate together with said transducers on a person;
operating said transducers to transmit pressure waves from said transducers into said person;
receiving pressure waves reflected from internal tissue structures of said person;
processing the pressure waves reflected from said internal tissue structures, to generate a virtual image or electronic model of said internal tissue structures;
deriving an image of said internal tissue structures from the virtual image or electronic model of said internal tissue structures; and
displaying the derived image for visual observation by a user or operator.

23. The method of claim 17 wherein said acoustic medium is taken from the group consisting of water and gel.

24. A method for generating an image of internal organs of a patient, comprising:
providing a carrier or substrate having a plurality of acoustic transducers disposable in contact with a skin surface of the patient, said carrier or substrate further including a plurality of metrologic devices;
placing said carrier on said skin surface so that said transducers are in pressure-wave-transmitting contact with the patient;
operating said metrologic devices to generate position data pertaining to relative positions of said transducers;
operating said transducers to generate acoustic data pertaining to internal tissue structures of the patient; and
processing said position data and said acoustic data to produce an image of said internal tissue structures.

25. The method of claim 24 wherein said carrier or substrate includes a plurality of rigid objects each carrying at least one of said transducers, said metrologic devices are disposed between respective pairs of said rigid objects, the operating of said metrologic devices including measuring increments in relative position and increments in relative orientation, further comprising determining an initial configuration of said array of objects and thereafter measuring a sufficient plurality of said increments to determine a global increment in a current configuration of said carrier or substrate.

26. The method of claim 25, wherein the determining of an initial configuration includes placing said rigid objects in contact with a body of known dimensions.

27. A method of calibrating an acoustic array, comprising:
(i) providing a body of known dimensions filled with an acoustic medium and containing a target of known acoustic properties at a pre-determined location inside said body;
(ii) placing an array of acoustic transducer assemblies in known positions and in operative contact with an exterior surface of said body;
(iii) providing a first system for determination of relative positions of said acoustic transducer assemblies;
(iv) providing a second system for generation of an image based on acoustic data transponded by said array of acoustic transducer assemblies and on said relative positions of the acoustic transducer assemblies;
(v) operating said first system for determination of said relative positions of said acoustic transducer assemblies;

(vi) generating a first correction based on comparison of said determination with said known positions;

(vii) operating said second system for generation of an image based on data transponded by said array of transducer assemblies and a corrected sense of said relative positions; and, (viii) generating a second correction based on comparison of said image with said pre-determined location of said target inside said body.

28. A method of determining a current configuration of an array of rigid objects, comprising:

(i) providing a set of metrologic devices disposed between members of a collection of pairs of said rigid objects, each of said devices operable to determine at least one of an increment in relative position and an increment in relative orientation, said collection of pairs chosen so that an exhaustive operation of said set of metrologic devices determines a sufficient number of said increments to uniquely determine a global increment in said current configuration of said array;

(ii) determining an initial configuration of said array of objects; and (iii) following said determining of an initial configuration, further determining by means of said set of metrologic devices a sufficient plurality of said increments to determine a global increment in said current configuration of said array, for determining, in conjunction with said determining of an initial configuration, a current configuration of said array.

29. The method of claim 28 wherein determining of an initial configuration includes placing rigid objects from said array of rigid objects in contact with a surface of a body of known dimensions.

30. The method of claim 29 wherein said rigid objects comprise acoustic transducers, and said determining of an initial configuration includes transmission and reception of acoustic signals, said signals having paths passing through said body of known dimensions.

31. A method of recording stereoscopic information, comprising;

(i) providing an array of acoustic transducers;

(ii) operating a first portion of said array to construct an acoustic image of a target from a first perspective; and (iii) operating a second portion of said array to construct an acoustic image of a target from a second perspective, objects imaged from said first perspective being at least partially identical with objects imaged from said second perspective.

32. The method of claim 31, further comprising electronically converting said acoustic image from a first perspective and said acoustic image from a second perspective to first and second optical images and providing said first and second optical images to respective eyes of an observer for simulation of binocular vision.

33. The method of claim 32 wherein the providing of said first and second optical images includes projecting said first and second optical images on a common optical plane.

34. The method of claim 32 wherein the providing of said first and second optical images includes using binocularly independent stereoscopic goggles.

35. The method of claim 31, further comprising storing or recording said first and second acoustic images for later retrieval for simulation of binocular vision.

\* \* \* \* \*